US012773135B2

(12) United States Patent
Emaminejad et al.

(10) Patent No.: US 12,773,135 B2
(45) Date of Patent: Oct. 27, 2026

(54) PROGRAMMABLE EPIDERMAL MICROFLUIDIC VALVING SYSTEM FOR WEARABLE BIOFLUID MANAGEMENT AND CONTEXTUAL BIOMARKER ANALYSIS

(71) Applicant: The Regents of the University of California

(72) Inventors: Sam Emaminejad, Los Angeles, CA (US); Haisong Lin, Los Angeles, CA (US); Jiawei Tan, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 984 days.

(21) Appl. No.: 17/394,208

(22) Filed: Aug. 4, 2021

(65) Prior Publication Data

US 2022/0061705 A1 Mar. 3, 2022

Related U.S. Application Data

(60) Provisional application No. 63/061,574, filed on Aug. 5, 2020.

(51) Int. Cl.
*A61B 5/145* (2006.01)
*A61B 5/00* (2006.01)
(Continued)

(52) U.S. Cl.
CPC ........ *A61B 5/14517* (2013.01); *A61B 5/0002* (2013.01); *A61B 5/259* (2021.01);
(Continued)

(58) Field of Classification Search
None
See application file for complete search history.

(56) References Cited

U.S. PATENT DOCUMENTS 6,626,417 B2 * 9/2003 Winger ............... F16K 99/0051 251/129.01
8,828,203 B2 * 9/2014 Bartetzko .......... G01N 27/3272 525/8
(Continued)

*Primary Examiner* — Michael R Bloch
(74) *Attorney, Agent, or Firm* — Foley & Lardner LLP

(57) ABSTRACT

Active biofluid management may be advantageous to the realization of wearable bioanalytical platforms that can autonomously provide frequent, real-time, and accurate measures of biomarkers in epidermally-retrievable biofluids (e.g., sweat). Accordingly, exemplary implementations include a programmable epidermal microfluidic valving system capable of biofluid sampling, routing, and compartmentalization for biomarker analysis. An exemplary system includes a network of individually-addressable microheater-controlled thermo-responsive hydrogel valves, augmented with a pressure regulation mechanism to accommodate pressure built-up, when interfacing sweat glands. The active biofluid control achieved by this system may be harnessed to create unprecedented wearable bioanalytical capabilities at both the sensor level (decoupling the confounding influence of flow rate variability on sensor response) and the system level (facilitating context-based sensor selection/protection). Through integration with a wireless flexible printed circuit board and seamless bilateral communication with consumer electronics (e.g., smartwatch), contextually-relevant (scheduled/on-demand) on-body biomarker data acquisition/display may be achieved.

17 Claims, 39 Drawing Sheets

A B

(51) Int. Cl.

| | |
|---|---|
| ***A61B 5/259*** | (2021.01) |
| ***B01L 3/00*** | (2006.01) |
| ***B01L 7/00*** | (2006.01) |
| ***C12N 9/02*** | (2006.01) |
| ***C12N 9/04*** | (2006.01) |
| ***G01N 1/14*** | (2006.01) |
| ***G01N 27/30*** | (2006.01) |
| ***G01N 27/327*** | (2006.01) |
| ***G01N 33/487*** | (2006.01) |
| *B82Y 40/00* | (2011.01) |

(52) U.S. Cl.

CPC ........ *A61B 5/681* (2013.01); *B01L 3/502707* (2013.01); *B01L 3/502715* (2013.01); *B01L 3/502738* (2013.01); *B01L 7/00* (2013.01); *C12N 9/0006* (2013.01); *C12N 9/0069* (2013.01); *G01N 1/14* (2013.01); *G01N 27/301* (2013.01); *G01N 27/3273* (2013.01); *G01N 33/48707* (2013.01); *B01L 2200/0689* (2013.01); *B01L 2300/0645* (2013.01); *B01L 2300/069* (2013.01); *B01L 2300/0819* (2013.01); *B01L 2300/0887* (2013.01); *B01L 2300/123* (2013.01); *B01L 2300/18* (2013.01); *B01L 2400/0478* (2013.01); *B01L 2400/06* (2013.01); *B82Y 40/00* (2013.01); *C12Y 101/03004* (2013.01); *C12Y 113/12004* (2013.01)

(56) References Cited

U.S. PATENT DOCUMENTS

2005/0090016 A1* 4/2005 Rich ........................ H01J 49/12 422/83
2006/0004271 A1* 1/2006 Peyser ............... A61B 5/14532 600/362
2007/0092407 A1* 4/2007 Xiao ................. B01L 3/502746 422/82.05
2007/0224241 A1* 9/2007 Stayton ............... C08F 293/005 525/158
2008/0280285 A1* 11/2008 Chen ................ G01N 35/00029 436/86
2009/0023610 A1* 1/2009 Peytavi ............ G01N 35/00029 422/240
2010/0156444 A1* 6/2010 Ponjee .................. B01L 3/5027 324/703
2010/0241241 A1* 9/2010 McKnight ................. A61F 2/04 623/24
2017/0296114 A1* 10/2017 Ghaffari ............. A61B 5/14517
2020/0000403 A1* 1/2020 Hussain ................. A61B 5/681

* cited by examiner

| Electronic components | Operation current | Required capacity |
|---|---|---|
| Potentiostat chip | 10 μA | 30 μA.h |
| MCU | 4 mA | 12 mA.h |
| Bluetooth | 5 mA | 15 mA.h |
| Heater | 100 mA | 20 mA.h |

Fig. 20a
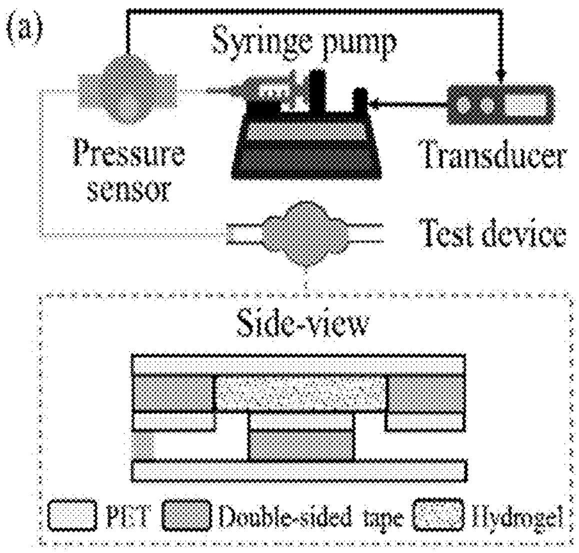
Fig. 20b
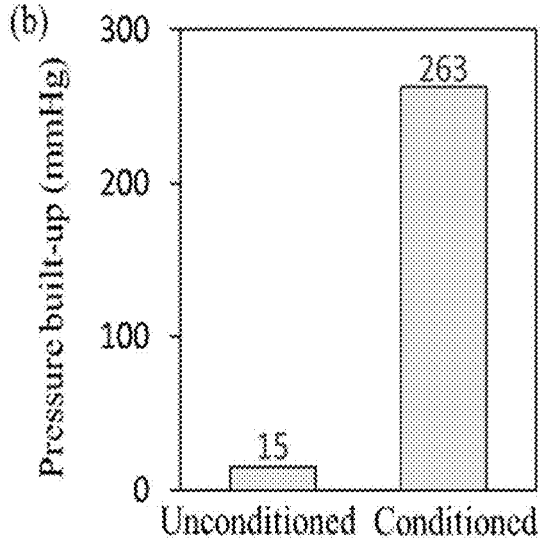
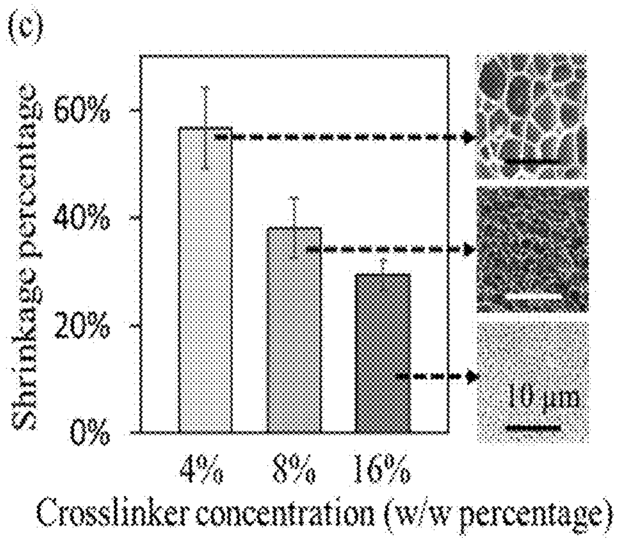
Fig. 20c
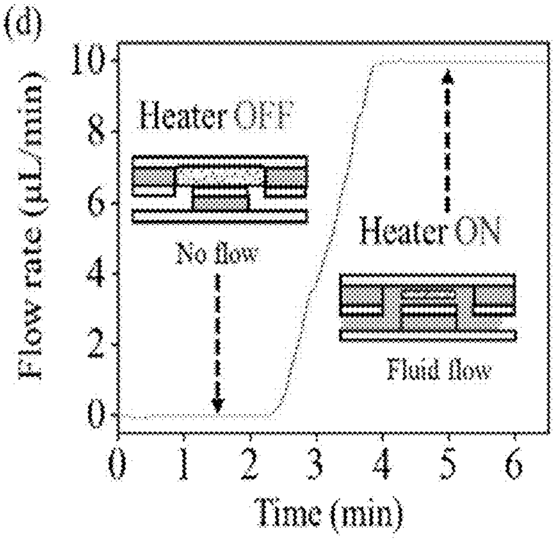
Fig. 20d

PROGRAMMABLE EPIDERMAL MICROFLUIDIC VALVING SYSTEM FOR WEARABLE BIOFLUID MANAGEMENT AND CONTEXTUAL BIOMARKER ANALYSIS

CROSS-REFERENCE TO RELATED APPLICATIONS

The present application claims priority to U.S. Provisional Patent Application No. 63/061,574 filed Aug. 5, 2020, the contents of which are incorporated herein by reference in their entirety.

STATEMENT REGARDING FEDERALLY SPONSORED RESEARCH OR DEVELOPMENT

The present embodiments were made with government support under Grant Number 1847729, awarded by the National Science Foundation. The government has certain rights in the invention.

TECHNICAL FIELD

The present implementations relate generally to wearable sensors, and more particularly to a programmable epidermal microfluidic valving system for wearable biofluid management and contextual biomarker analysis.

BACKGROUND

Lack of active control on biofluid flow fundamentally renders conventional devices 1) susceptible to operationally relevant confounders such as flow rate variability, 2) incapable of performing diverse bioanalytical operations (e.g., incubation), and 3) incapable of delivering programmable biofluid management functionalities (e.g., biofluid routing and compartmentalization) that are critical to the operational autonomy of advantageous systems, such as capturing biomarker readings at contextually-relevant timepoints.

It is against this backdrop that the present Applicant sought to advance the state of the art.

SUMMARY

Active biofluid management may be advantageous to the realization of wearable bioanalytical platforms that can autonomously provide frequent, real-time, and accurate measures of biomarkers in epidermally-retrievable biofluids (e.g., sweat). Accordingly, exemplary implementations include a programmable epidermal microfluidic valving system capable of biofluid sampling, routing, and compartmentalization for biomarker analysis. An exemplary system includes a network of individually-addressable microheater-controlled thermo-responsive hydrogel valves, augmented with a pressure regulation mechanism to accommodate pressure built-up, when interfacing sweat glands. The active biofluid control achieved by this system may be harnessed to create unprecedented wearable bioanalytical capabilities at both the sensor level (decoupling the confounding influence of flow rate variability on sensor response) and the system level (facilitating context-based sensor selection/protection). Through integration with a wireless flexible printed circuit board and seamless bilateral communication with consumer electronics (e.g., smartwatch), contextually-relevant (scheduled/on-demand) on-body biomarker data acquisition/display may be achieved.

To this end, valving may be advantageous to active biofluid management, because it enables flow control. The significance of valving is notable in microfluidic-based lab-on-a-chip platforms. Specifically, programmable valving systems may deliver active manipulation and control of small-scale (~nano/microliter) fluid flow within networks of microfluidic channels, forming separated compartments to perform biochemical reactions in an addressable manner. Such valving systems may execute synchronous/asynchronous sequential and parallel fluid manipulation tasks autonomously, leading to the creation of new microfluidic solutions for various applications including diagnostics and -omics. Conventional programmable valving systems have not been adapted for integration into lab-on-the-body-like wearable platforms, which may be primarily due to the bulkiness of the actuation instruments (e.g., external mechanical pumps). Conventional valving interfaces of wearable platforms embedded within sophisticated flexible epidermal microfluidic configurations are either passive or require manual mechanical activation.

BRIEF DESCRIPTION OF THE DRAWINGS

These and other aspects and features of the present implementations will become apparent to those ordinarily skilled in the art upon review of the following description of specific implementations in conjunction with the accompanying figures, wherein:

FIG. 1*a* illustrates an exemplary wearable bioanalytical platform, including an integrated programmable microfluidic valving system interfacing a flexible printed circuit board (FPCB). FIG. 1*b* illustrates an exemplary poly(N-isopropylacrylamide) (PNIPAM) PNIPAM hydrogel shrinkage/expansion in response to temperature change above/below its lower critical solution temperature (LCST) (induced by activation/deactivation of the microheater). FIG. 1*c* illustrates an exemplary schematic operation example of the programmable microfluidic valving system, demonstrating biofluid routing, compartmentalization, and analysis in the selected compartment and sensor protection in the non-selected compartments. FIG. 1*d* illustrates exemplary control commands (automated and manual) communication for scheduled and on-demand biomarker data acquisition with the aid of user interfaces preloaded on smart consumer electronics.

FIG. 2*a* illustrates exemplary PNIPAM hydrogel shrinkage percentage vs. temperature profile. Microscopic images of the hydrogel at the annotated temperatures are shown as insets. FIG. 2*b* illustrates an exemplary reversible hydrogel volume transition upon activation and deactivation of an exemplary microheater. FIG. 2*c* illustrates a microfluidic valving characterization setup with a feedback-controlled pressure configuration. FIG. 2*d* illustrates an exemplary measured flow rate profile through a valve-gated microfluidic channel upon periodic activation/deactivation of an exemplary valve. FIG. 2*e* illustrates an exemplary hydrogel layer fabrication procedure and layer-by-layer device integration scheme to realize microfluidic valving systems with different architectures. FIG. 2*f* illustrates optical images of exemplary fabricated hydrogel layers with different numbers/arrangements of hydrogels (a black substrate background may be used to visualize the transparent hydrogel features). FIG. 2*g* illustrates sequential optical images of exemplary progressive microfluidic routing and compartmentalization through illustrative serial, parallel, and tree microfluidic networks (constructed through integration with an exemplary same arrangement of hydrogels).

FIG. 3*a* illustrates an exemplary electric-hydraulic analogy, where $V_{min}$ represents exemplary minimum turn-on voltage of the transistor switch; $V_{max}$ represents exemplary maximum tolerable voltage of the transistor switch; $P_{min}$ represents exemplary minimum pressure to open the valve; and $P_{max}$ represents exemplary maximum tolerable pressure of the hydraulic valve). FIG. 3*b* illustrates an exemplary design rationale of an exemplary pressure regulation mechanism (assisted by the exemplary electrical circuit analogy). FIG. 3*c* illustrates an optical image of an exemplary implemented pressure regulated valve. FIGS. 3*d-f* illustrate exemplary characterization of (d) maximum tolerable pressure, (e) minimum pressure, and (f) regulated pressure. Input flow rate may be set to 5 μL/min. FIG. 3*g* illustrates exemplary characterized accumulated pressure across pressure regulated-microfluidic channels at different exemplary flow rates (error bars indicate standard error, n=3). FIG. 3*h* illustrates exemplary sequential optical images of progressive microfluidic routing and compartmentalization through an exemplary pressure-regulated six-compartment valving system (performed ex-situ, by way of example).

FIG. 4*a* illustrates an exemplary reaction schematic of an exemplary developed sensor (embedded within a valve-gated compartment, by way of example). FIGS. 4*b* and 4*c* illustrate an exemplary response to target analytes for (b) a glucose sensor and (c) a lactate sensor. Exemplary error bars indicate standard error. In some implementations, standard error is n=3 different sensors. FIG. 4*d* illustrates exemplary simulated analyte concentration (gradient) profiles for relatively low and high flow rate conditions (low flow rate: Q=1 μL/min, resulting in Pe=12.4, high flow rate: Q=10 μL/min, resulting in Pe=124, assuming a channel transverse width of 2 mm and analyte diffusivity constant of $6.7\times10^{-6}$ $cm^2/s$). Exemplary annotated dashed lines tangent to the normalized concentration curves indicate the local analyte concentration gradient for the respective case. FIG. 4*e* illustrates an exemplary simulated local analyte concentration gradient at various flow rates (exemplary values are normalized to that obtained for the exemplary case of 1 μL/min). An exemplary curve fitted line indicates that simulated data points present a $\sqrt[3]{Q}$ relationship. FIG. 4*f* illustrates an exemplary measured amperometric current response of a glucose sensor to 200 μM glucose solution introduced at various flow rates. The inset figure shows a corresponding exemplary measured real-time amperometric current response in the presence of progressively increasing flow rate (from 0 to 10 μL/min). The exemplary curve fitted line indicates that simulated data points present a $\sqrt[3]{Q}$ relationship. FIG. 4*g* illustrates an exemplary comparison of the estimated glucose concentration of a 200 μM glucose solution introduced at 5 μL/min (no valve) and 0 μL/min (corresponding to an exemplary valve-gated condition). Error bars indicate standard error (n=3).

FIG. 5*a* illustrates exemplary ex situ characterization of exemplary prolonged operation of the pressure-regulated valve (performed over six hours, by way of example). FIG. 5*b* illustrates exemplary ex situ characterization of exemplary high-fidelity operation of the pressure-regulated valve in the presence of vortical vibration. Exemplary vibrational acceleration profiles are presented in the top half, and exemplary characterized flow rate profile may be captured in the bottom half. FIG. 5*c* illustrates an optical image of an exemplary fully integrated programmable epidermal microfluidic valving system applied on the back of a subject with a zoomed-in view of exemplary FPCB electronic components. The block diagram details an exemplary circuit-level valve actuation and signal processing operations. FIG. 5*d* illustrates an exemplary process for scheduled/on-demand sweat sampling during physical activity (cycling). FIG. 5*e* illustrates optical images of exemplary intermittently sampled, routed, and compartmentalized sweat on-body (visualized by way of example with the aid of blue dyes, embedded within the compartments). Three valves may be sequentially activated and deactivated at programmed timepoints during a physical exercise. The inset figures show exemplary characterized electrical current through the respective valves' microheaters (activated for four minutes by way of example). FIG. 5*f* illustrates exemplary on-body sensor readouts and the corresponding exemplary calibration curves. Sweat glucose readouts may be obtained by the valve-gated sensing compartments 1 and 2, before and after a scheduled beverage intake event, respectively. An exemplary sweat lactate readout may be obtained by the valve-gated sensing compartment 3 upon on-demand user activation.

FIGS. 20*a*-20*d* illustrate an exemplary sensor and aspects thereof. FIG. 20*a* illustrates an exemplary pressure sensor-coupled syringe pump system. FIG. 20*b* illustrates an exemplary back pressure characterization of hydrogel valves, fabricated with and without a conditioning step. FIG. 20*c* illustrates exemplary shrinkage percentage of hydrogels, fabricated with different crosslinker concentrations (with an exemplary n=3, and error bars indicating standard error). Insets show the SEM images of the corresponding exemplary hydrogels. In some embodiments, the lower the crosslinker concentration, the larger the resultant pores in the hydrogel structure, leading to the higher rate of water molecule diffusion and the larger hydrogel volumetric response to temperature changes. FIG. 20*d* illustrates exemplary characterization of flow rate through a hydrogel valve-gated microfluidic channel. Upon turning the heater on, and subsequent hydrogel shrinkage, the fluid will flow in the channel and pass through the valve chamber through vertically aligned VIAs (vertical interconnect accesses).

FIGS. 22*a-c* illustrate exemplary fluid routing within a square matrix microfluidic network. FIG. 22*a* illustrates an exemplary addressable on-board heater array. In some embodiments, multiplexers facilitate electrical connections of the selected valve's heater terminals. FIG. 22*b* illustrates a side-view an exemplary valve-gated microfluidic channel and heater interface. FIG. 22*c* illustrates sequential optical images of fluid routing through an exemplary zigzag path. FIGS. 22*d-f* illustrate fluid routing and compartmentalization within an exemplary radial tree matrix microfluidic network. FIG. 22*d* illustrates an exemplary addressable flexible (PET-based) heater. FIG. 22*e* illustrates a side view of an exemplary valve-gated and heater-integrated microfluidic module. In some embodiments, heaters are electrically connected to control electronics via an incorporated anisotropic conductive film (ACF) layer. FIG. 22*f* illustrates sequential optical images of exemplary fluid routing and compartmentalization.

DETAILED DESCRIPTION

Figure 1B:
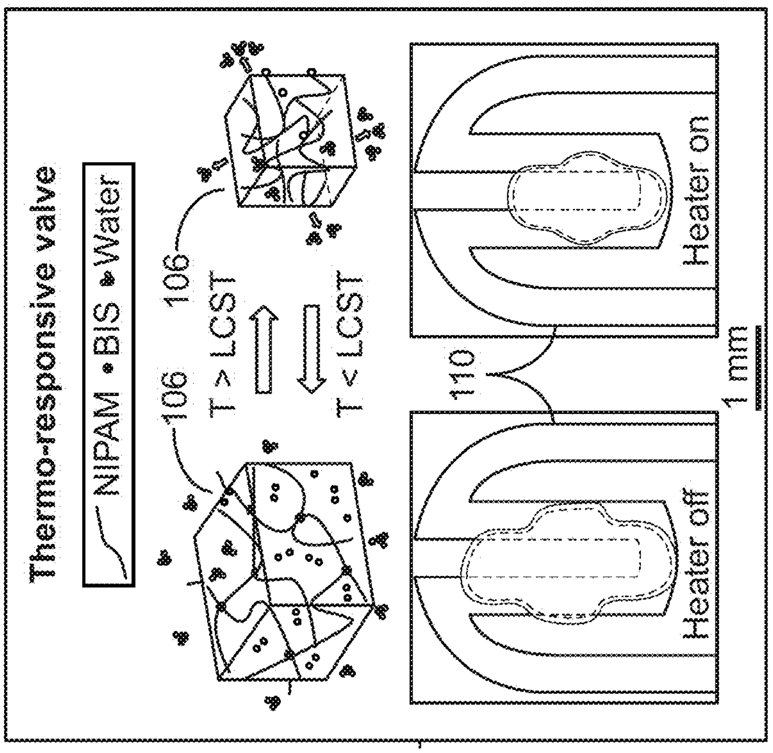
FIGS. 1*a*-1*d* illustrate an exemplary fully-integrated wearable valving system (concept and operational principle).

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of inter-change of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Wearable biomarker sensing technologies enable personalized and precision medicine by allowing the frequent, longitudinal, and comprehensive assessment of an individual's health. Recent advances in biochemical sensor development, device fabrication and integration technology, and low-power electronics have paved the path for the realization of wearable systems, capable of analyzing epidermally-retrievable biofluids (e.g., sweat), to access molecular-level biomarker information. Wearable biomarker sensors may be advantageous for electrochemical and colorimetric sensing interfaces for the on-body detection of analytes. These sensors rely on the analysis of biofluid samples that are passively collected in predefined microfluidic structures to minimize evaporation.

Conventional devices are not suitable for integration into lab-on-the-body-like wearable platforms, due at least partially to the bulkiness of actuation instruments, including but not limited to, external mechanical pumps and optical excitation systems.

Exemplary implementations include a wearable and programmable biofluidic management system for biomarker analysis, which autonomously routes and compartmentalizes biofluids (e.g., sweat) in addressable sensing chambers. Active biofluid management may be advantageous to the realization of wearable biomarker sensing platforms. Despite the fact that such platforms may autonomously provide frequent, real-time, and accurate measures of diverse biomarkers-inherently necessitating active functionalities-all the presented wearable biomarker sensing platforms are implemented by passive components and static structures (e.g., absorbent pads or microfluidic housing). To address this technological gap, exemplary implementations include a valving system, and a network of individually-addressable microheater-controlled thermo-responsive hydrogel valves. To embody an exemplary valving system for harvesting sweat, interstitial fluid, or the like, from high-pressure secreting glands, an electronic-hydraulic analogy may be formulated, which may inform the design of pressure regulating implementations to accommodate pressure built-up. Exemplary implementations include a circuit-controlled micropatterned heater (on a flexible substrate) to actuate the hydrogels. In this way, we formed a miniaturized programmable valve, which can be extended into an addressable array, and subsequently, exploited to realize a valve-gated multicompartment bioanalytical platform amenable for wearable applications.

The active fluid control achieved by exemplary implementations may be harnessed to create new wearable bioanalytical capabilities at both the sensor and system levels. At the sensor level, exemplary valving may decouple the confounding influence of flow rate variability on the sensor response: an issue which may be overlooked by previously reported wearable sensors. At the system level, the addressable biofluid routing/compartmentalization capability may be achieved by valving, to implement programmable sensor selection/protection, where the mode of analysis can be selected depending on the user's need, behavior, and activity. Through integration with a wireless printed circuit board and bilateral seamless communication with consumer electronics, an exemplary valving system may be applied to perform contextually-relevant (scheduled/on-demand) on-body biomarker data acquisition. Active biofluid management within the framework of wearable biosensing systems in accordance with present implementations support fully autonomous lab-on-body-like technologies which are poised to transform personalized and precision medicine.

To render active biofluid management in a wearable format, here, an exemplary electronically-programmable microfluidic valving system, may be capable of biofluid sampling, routing, and compartmentalization for biomarker analysis. An exemplary microfluidic system may include a network of individually-addressable microheater-controlled thermo-responsive poly(N-isopropylacrylamide) (PNIPAM) hydrogel valves. A simple, high-throughput, and low-cost fabrication scheme may develop hydrogel arrays on a tape-based flexible substrate. The fabricated hydrogel arrays can be incorporated within a 3D flexible microfluidic module, following an extensible vertical integration scheme, which allows for the assembly of microfluidic implementations and actuation/sensing electrode arrays within a compact footprint. To adapt the valving system for on-body biofluid harvesting, specifically, in the context of interfacing with pressure-driven bio-interfaces (e.g., sweat glands), exemplary implementations may include a pressure regulation mechanism, informed in some implementations by an electronic-hydraulic analogy.

An active fluid control achieved by this system may be harnessed to create new wearable bioanalytical capabilities at both the sensor and system levels. At the sensor level, an exemplary valving capability may be exploited to decouple the confounding influence of flow rate variability on the sensor response. At the system level, valving may be leveraged in some implementations to render addressable biofluid routing and compartmentalization. These capabilities can be positioned to render context-based sensor selection/protection, where the mode of analysis may be selected depending on the user's need, behavior, and activity.

To deliver seamless control command and biomarker data communication, an exemplary sensor array-coupled valving system may interface with a custom-developed wireless flexible printed circuit board (FPCB), equipped with multi-channel valve-actuation and signal processing capabilities. In some implementations, through bilateral Bluetooth® communication with a portable device such as a smart phone or smartwatch, preloaded with a custom-designed user interface, biomarker data acquisition and display at scheduled/on-demand timepoints may be achieved. An exemplary complete wearable valve-enabled bioanalytical platform may take selective biomarker readings, on-body, at various contextually-relevant timepoints.

Exemplary Implementations

Figure 1A:
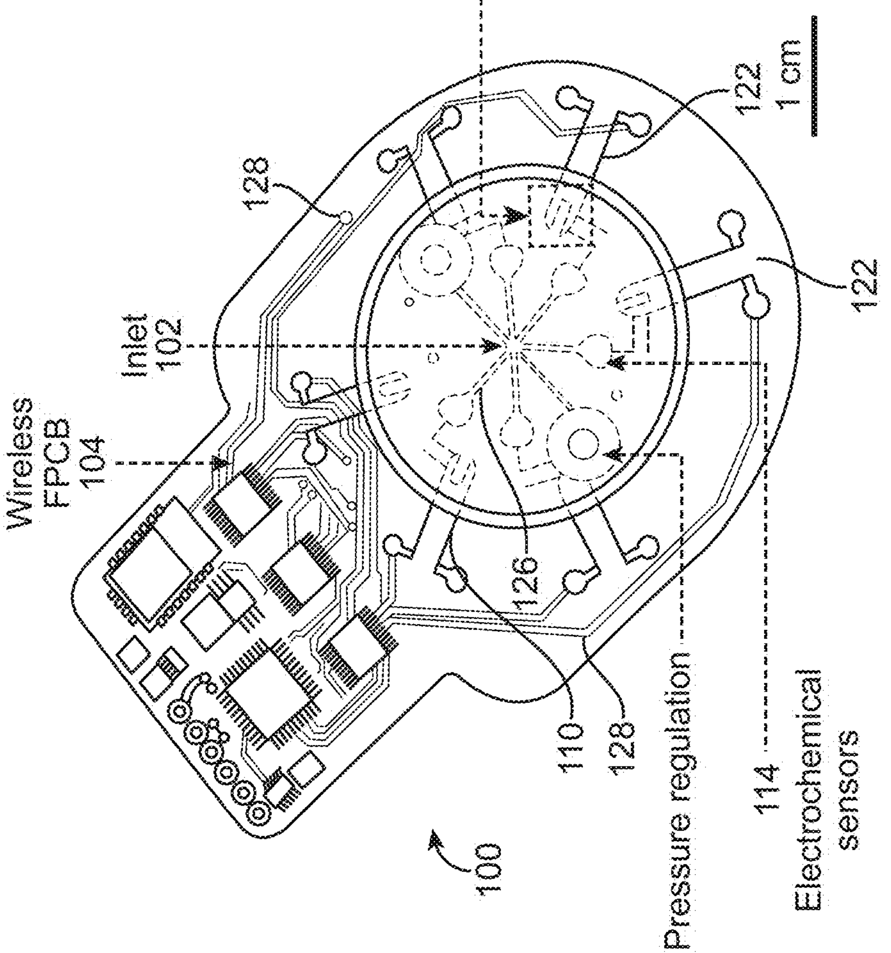
Figure 6C:
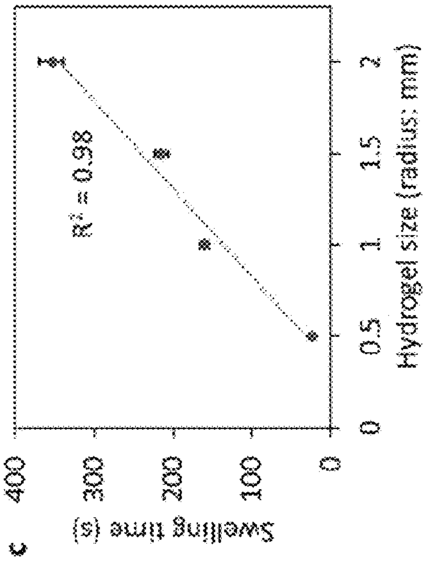
FIGS. 6*b* and 6*c* illustrate exemplary characterization of the hydrogel volume transition time vs hydrogel size upon activation and deactivation of the microheater for shrinkage (b) and swelling (c). Shrinkage and swelling times are defined by way of example as the time it takes for the hydrogel shrinkage/expansion to settle within 1% of its steady-state volume upon (activation/deactivation of the microheater). Error bars indicate standard error (n=3).
Figure 6B:
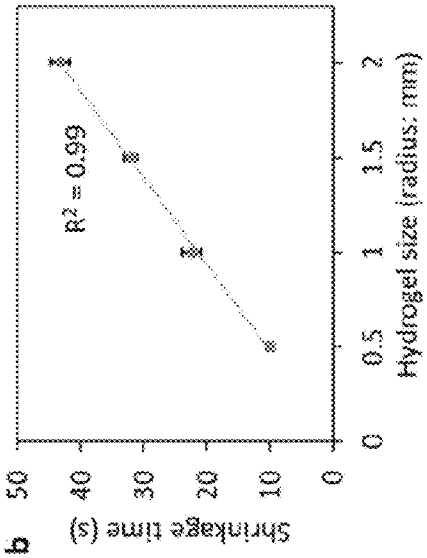
Figure 6A:
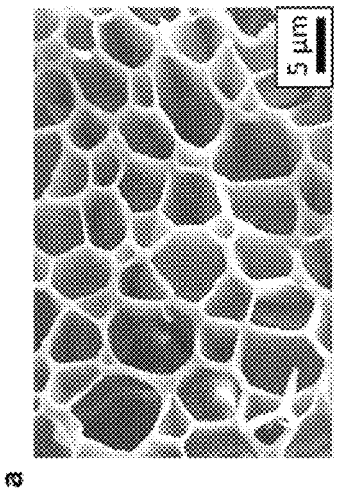
FIG. 6*a* illustrates an exemplary Scanning Electron Microscopy (SEM) image of an exemplary freeze-dried hydrogel with 4% BIS.

Exemplary operational principles of an exemplary fully-integrated wearable valving system will now be described. FIG. 1*a* illustrates an exemplary pressure-regulated six-compartment valving system 100 with a sweat collection inlet 102 at the center and an electrochemical sensing interface 114 within each compartment 122 coupled to the inlet via a microfluidic channel 126 and a valve-interfacing via signal lines 128 to a wireless flexible printed circuit board (FPCB) 104 to form a fully-integrated wearable bioanalytical platform. An exemplary valve includes a PNIPAM-based hydrogel 106 as shown in FIGS. 1*b* and 6*a*, synthesized from a NIPAM monomer and N,N'-methylenebis(acrylamide), BIS crosslinker), which significantly shrinks/expands in response to local temperature increments/decrements, above/below its lower critical solution temperature (LCST).

Figure 1C:
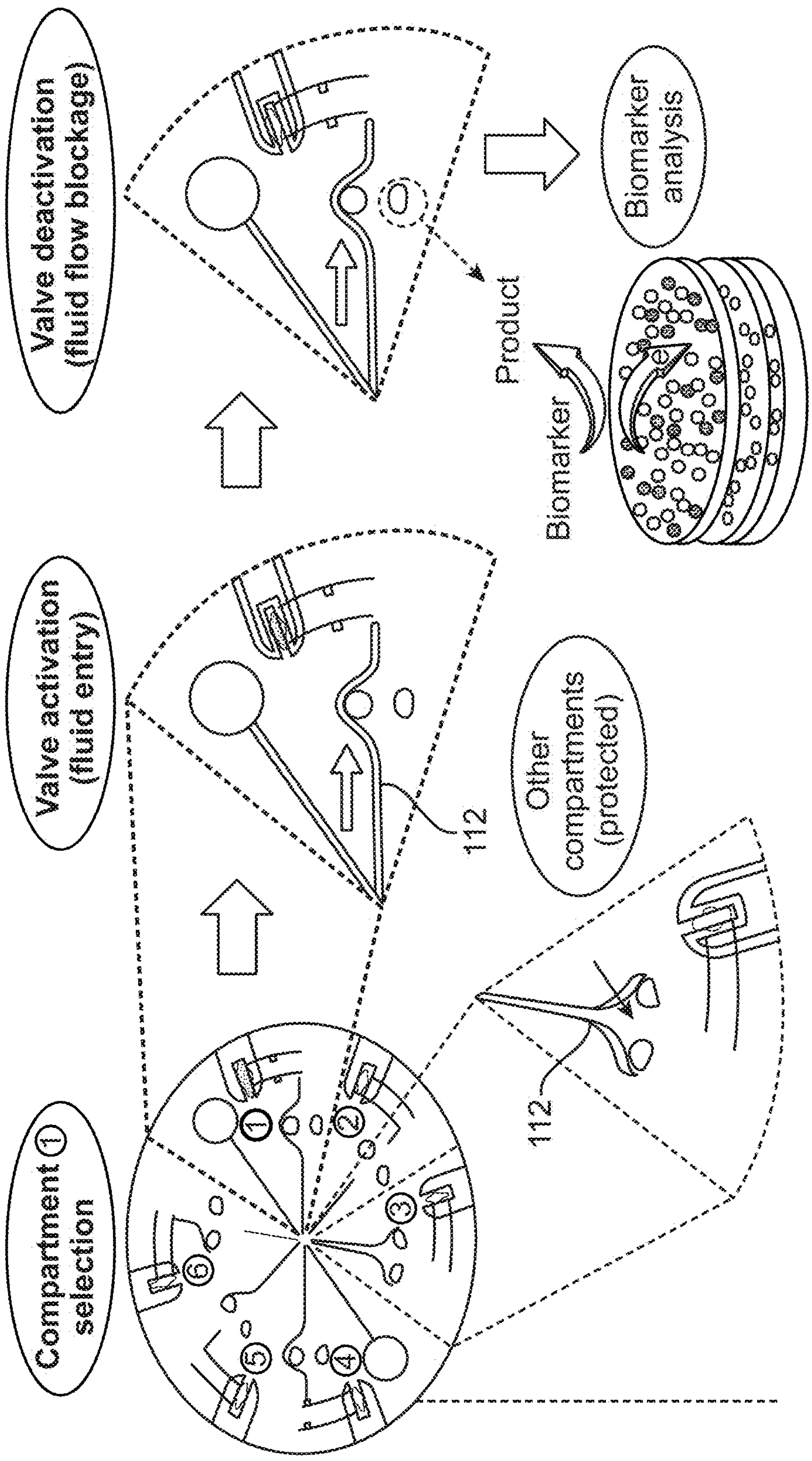

In some implementations, by embedding this hydrogel 106 within a microfluidic channel 126, and with the aid of a circuit-controlled micropatterned heater 110 in each compartment, the volumetric thermal responsiveness of the hydrogel 106 can be exploited to effectively permit/block fluid flow via activation and deactivation of the heater 110. As shown in FIG. 1*c*, a programmable valve 112 may thus be formed, which can be extended into an addressable array, and subsequently, exploited to realize a valve-gated multi-compartment bioanalytical platform. An example operation of such a system is shown in FIG. 1*c*. In this example and as shown in the left and center portion of FIG. 1*c*, the valve 112 (downstream of the microfluidic channel) in compartment 1 may be first activated (while others remain deactivated) to route and sample biofluid. Then as shown in the right portion of FIG. 1*c*, it may be deactivated to block the flow, allowing for biofluid compartmentalization and analysis (using an electrochemical sensor 114 positioned upstream of the channel). Accordingly, sample analysis can be performed-without the confounding influence of flow rate variability—by the sensor(s) 114 in the addressed compartment, while the sensors 114 in the other compartments remain protected.

Figure 1D:
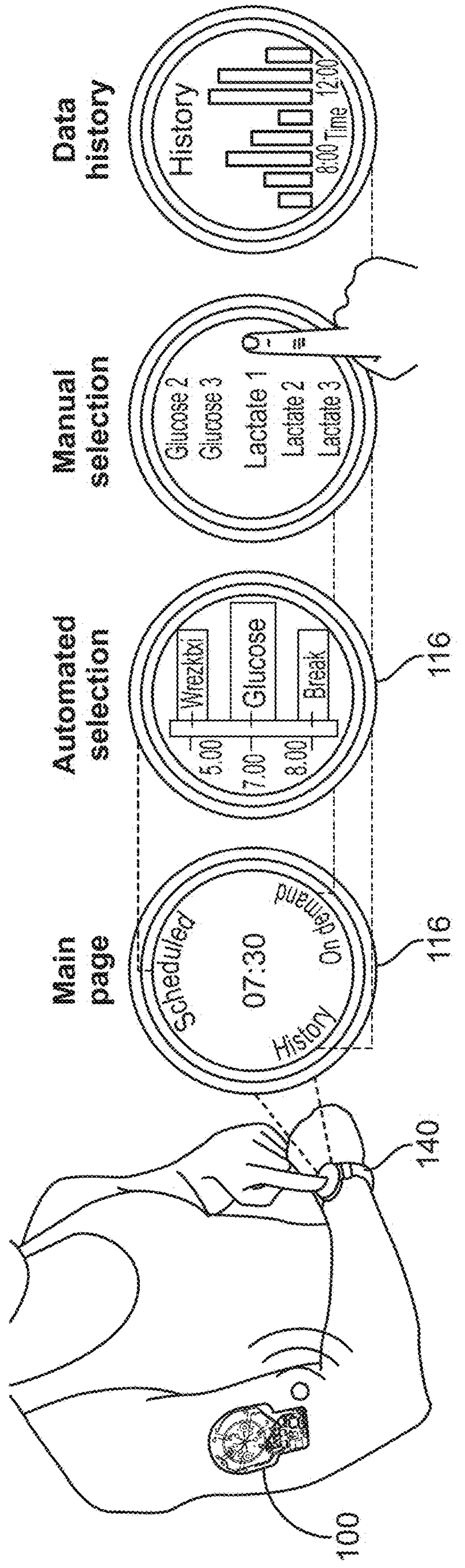

In some implementations, an addressable compartmentalization capability can be exploited to take biomarker readings at scheduled/on-demand timepoints, thus enabling contextual biomarker analysis. In an exemplary wearable bioanalytical platform 100, valve activation and sensor output signal processing are delivered with the aid of a circuit board 104, which may be equipped with a multi-channel programmable current source and analog front-end circuits. Through bilateral Bluetooth® communication with personal smart electronics (e.g., smartwatch 140), preloaded with a custom-designed user interface 116, biomarker data acquisition timepoints (pre-scheduled/on-demand) can be programmed (via automated/manual commands) and biomarker data can be displayed in real-time as shown in FIG. 1*d*.

Exemplary fabrication and characterization aspects of wearable valve-gated microfluidic networks will now be described. For fluid valving, ideally, a binary off/on valve operation may be desired, where fluid flow may be completely blocked with no leakage in the "off"-state (when the valve may be deactivated), and fluid flow may be permitted in the "on"-state (when the valve may be activated). In the context of exemplary thermo-responsive PNIPAM-based hydrogel 106, off/on transition may be achieved upon decreasing/increasing the temperature below/above the LCST as shown in FIG. 1*b*. The thermo-responsive property of PNIPAM stems from the coexistence of hydrophilic amide and hydrophobic propyl groups within its polymer structure. When the hydrogel's temperature may be lower than its LCST, the hydrogen-bonding interactions between the amide group and the water molecules may be dominant. Therefore, the hydrogel 106 may become highly hydrated, leading to its structural expansion. Conversely, when the hydrogel's temperature may be higher than its LCST, the hydrogen-bonding interactions may become weaker and the interactions between the hydrophobic propyl group and the water molecules may be dominant. As a result, the water may be released from the hydrogel 106 structure, leading to hydrogel shrinkage.

Figure 2B:
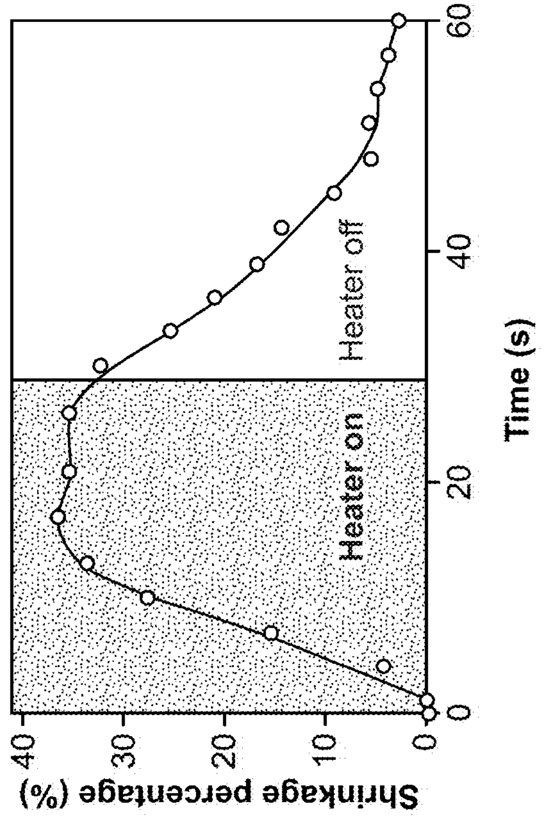
FIGS. 2*a*-2*g* illustrate exemplary fabrication and characterization of valve-gated microfluidic networks.
Figure 2A:
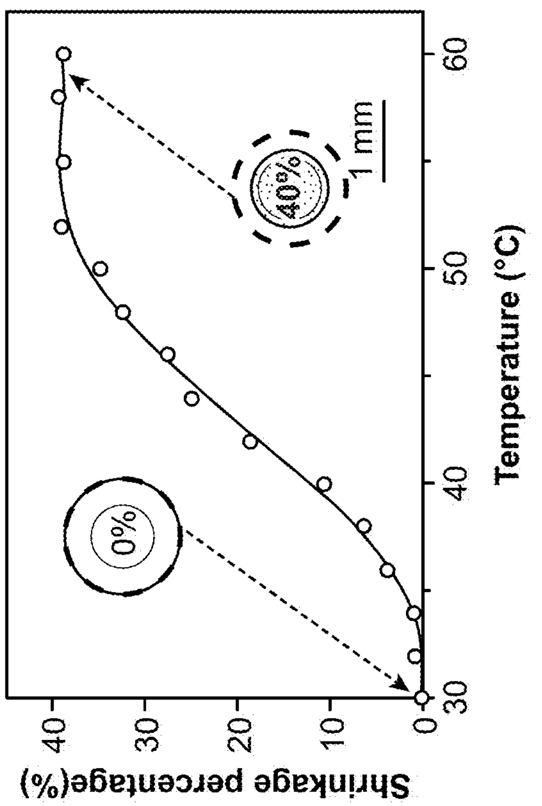

For robust on-body valving, the temperature at which the hydrogel's volumetric transition occurs should, in some implementations, be sufficiently above the skin temperature (~35° C.), such that the heat transfer from the skin to the valve does not result in significant hydrogel shrinkage and subsequent fluid leakage. By incorporating an ionizable monomer (e.g. [3-(methacryloylamino)propyl]trimethylammonium chloride (MAPTAC)) in an exemplary hydrogel structure, exemplary volumetric transition temperature of about 45° C. may be achieved. As shown in FIG. 2*a*, an exemplary modified PNIPAM-based hydrogel exhibits about 40% shrinkage from its original size (based on the 2D imaged area) after ramping up its temperature above the LCST point. As illustrated in FIG. 2*b*, the hydrogel can recover back to its original volume, simply by deactivating the microheater at a later point in time. The observed asymmetry in the hydrogel shrinkage and recovery rates can be attributed to the difference between the outward and inward diffusion rates of the surrounding buffer solution that may be leaving and entering the hydrogel, respectively. Moreover, exemplary corresponding shrinkage and recovery rates may be proportional to the hydrogel size as illustrated in FIGS. 6*b* and 6*c*.

Figures 2C, 2D:
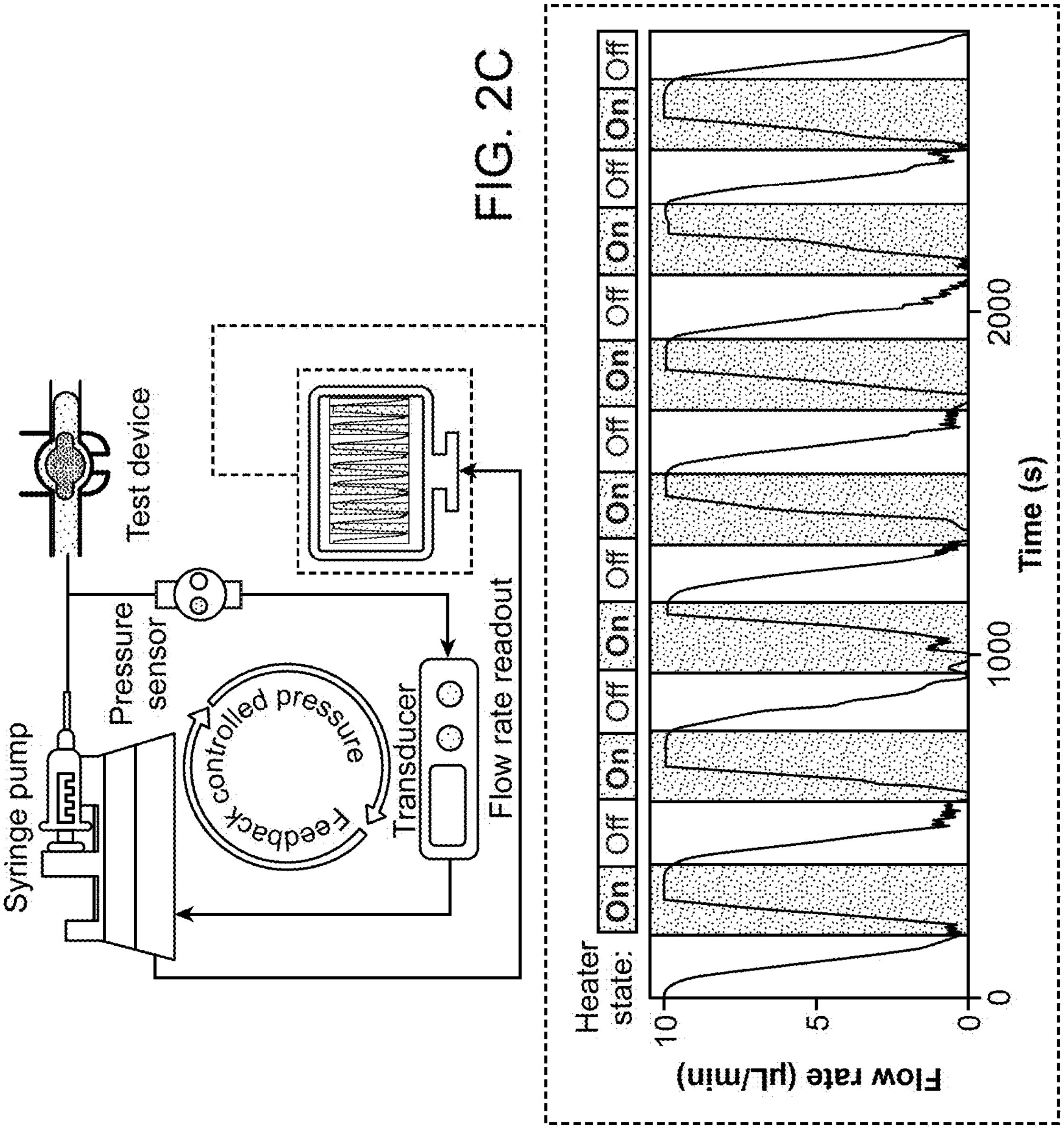
Figure 12:
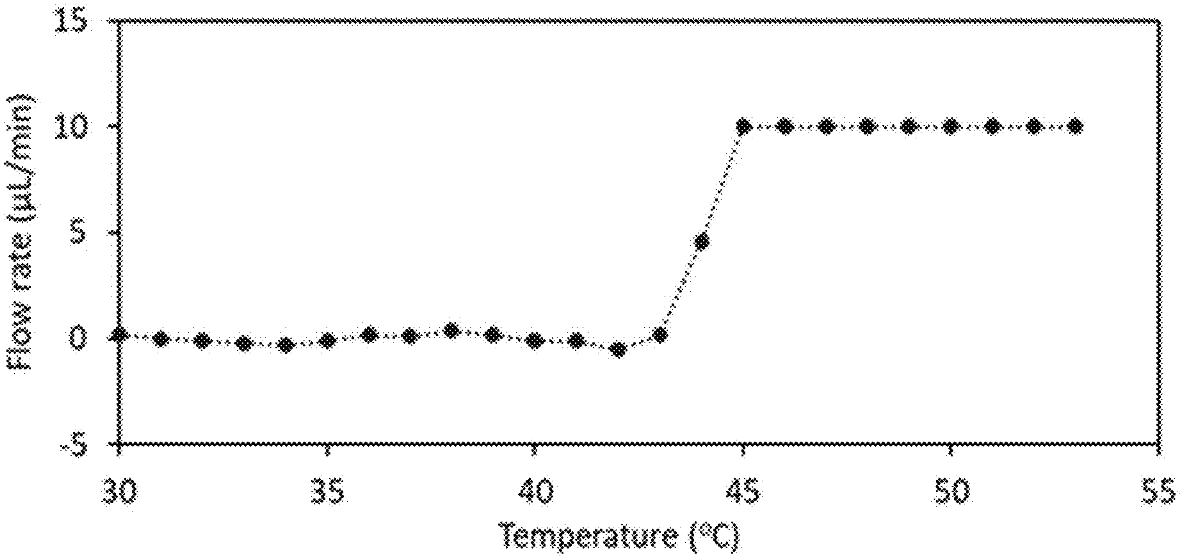
FIG. 12 illustrates an exemplary flow rate vs. hydrogel valve temperature profile at an exemplary pressure set as 15 mmHg. An exemplary valve is opened when the temperature exceeds 44° C. The Y-axis indicates exemplary averaged continuous recordings of the flow rate for each temperature condition.

In order to maintain a fast valve responsive time, exemplary implementations may minimize the size of the hydrogel embedded inside the channel (circle-shaped with radius<1 mm). By setting up a pressure-controlled fluid flow testing configuration as shown in FIG. 2*c*, the flow rate within a hydrogel-embedded and microheater-coupled microfluidic channel may be monitored. As shown in FIG. 2*d*, upon deactivation/activation of the microheater, an exemplary flow rate within the channel may correspondingly drop to zero/recover to its default value, illustrating the reversible, consistent, and periodic switching capabilities of a formed valve in accordance with present implementations. An exemplary slower transient characteristic of an exemplary embedded hydrogel as compared to that of an exemplary standalone hydrogel (by comparison of FIG. 2*b* vs. FIG. 2*d*) can be attributed to the surface contact forces acting on the embedded hydrogel. Furthermore, an exemplary device includes a temperature characterization showing that—operationally—the valve opens at temperatures greater than or equal to about 45° C. (see, e.g., FIG. 12).

Figure 2E:
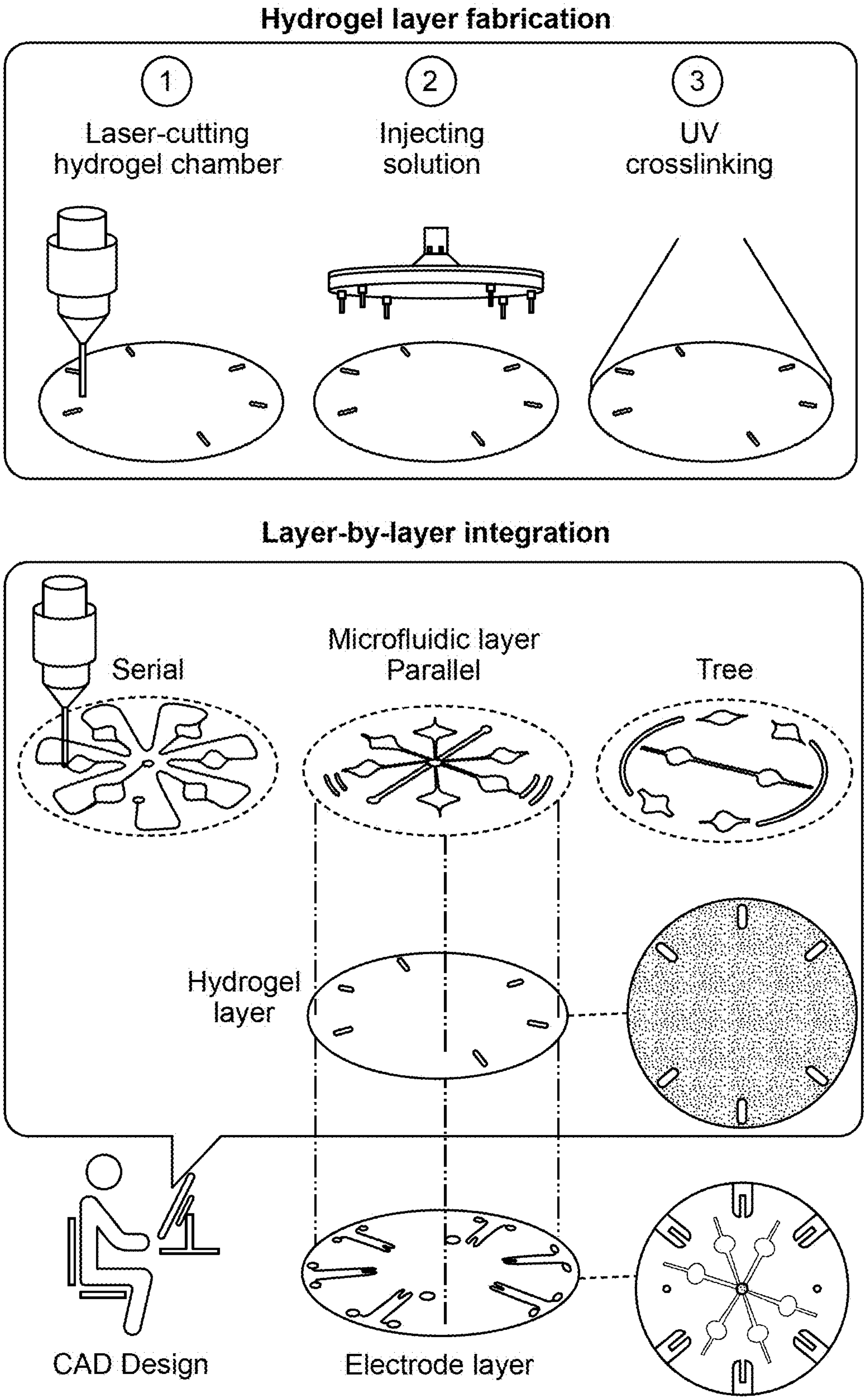
Figure 2F:
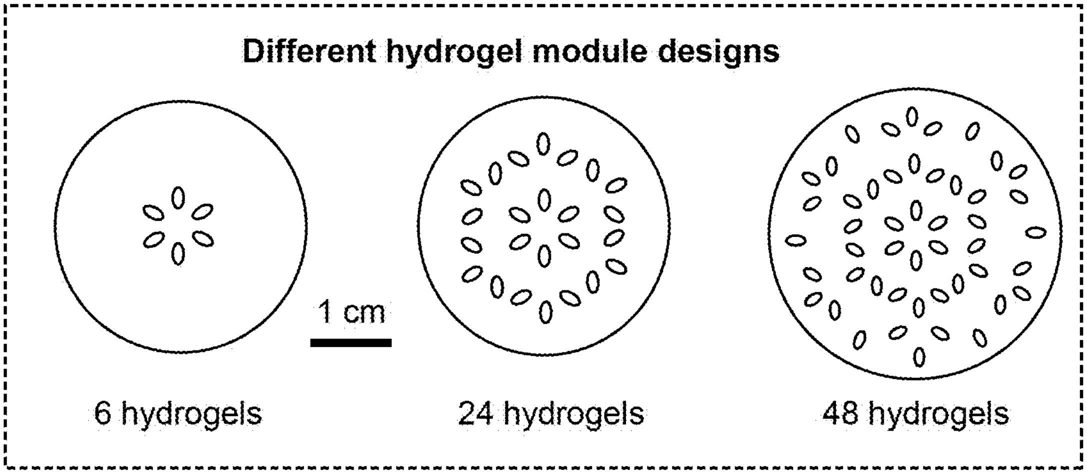
Figure 2G:
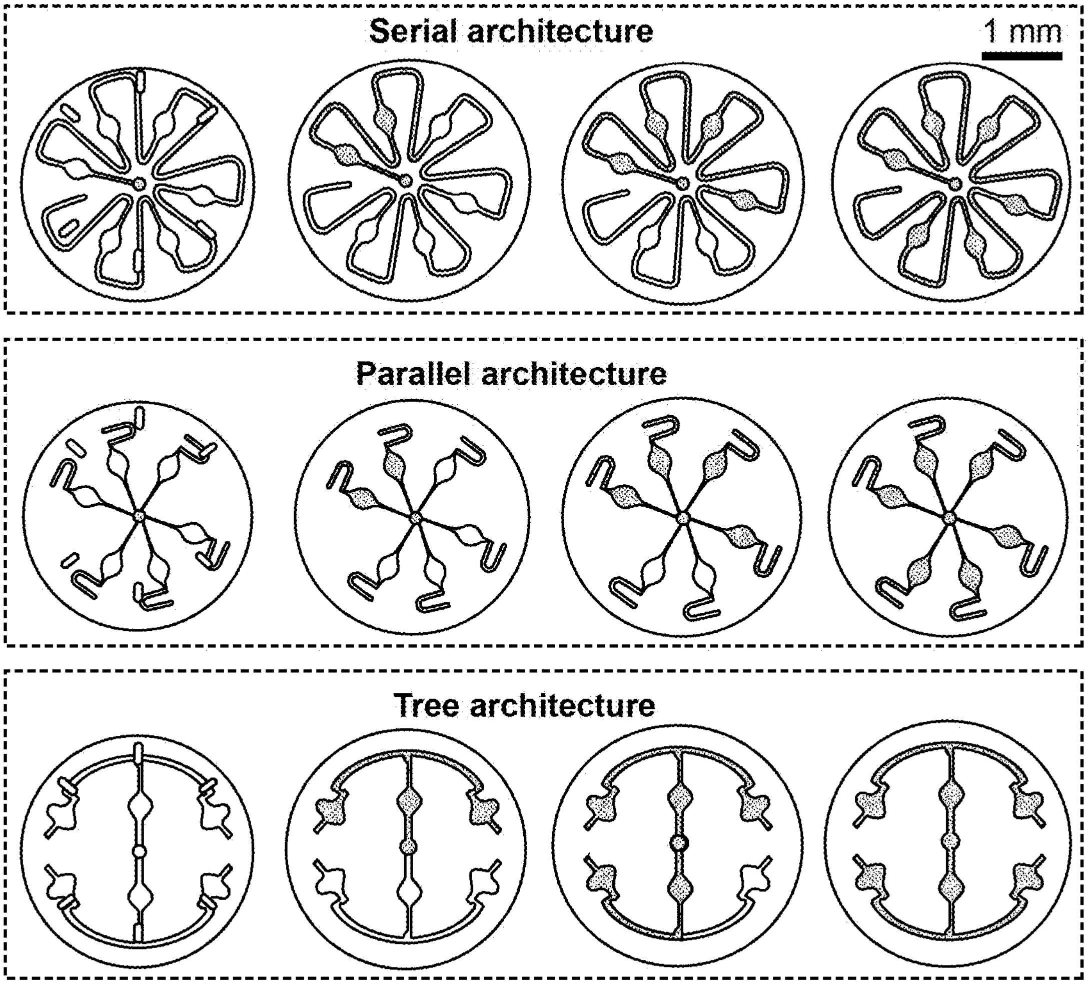

In some implementations, the valve interface may be fabricated in an array format and within a tape-based flexible microfluidic module. A simple and high-throughput fabrication and integration scheme may thus be embodied. One exemplary process shown in FIGS. 2*e*, 7 and 8 includes fabricating the hydrogel array, microfluidic network structure, and electrode array on separate layers, followed by vertical alignment and assembly of the layers. An exemplary microheater electrode array layer is positioned as a top layer. In some implementations, the electrode array layer is positioned away from the skin where the intermediary layers serve as insulators, to minimize the heat conduction to skin. An exemplary hydrogel array and microfluidic network features may be defined by a laser-cutter, which can be programmed at a software level to rapidly render various arrangements and dimensions. Exemplary hydrogel arrays can be developed by simultaneously injecting PNIPAM precursor solutions into the respective defined features, followed by a one-step ultraviolet crosslinking procedure, altogether rendering the development process low-cost and highly scalable in terms of number of hydrogel modules as illustrated in FIG. 2*f*. An exemplary vertical integration approach may also allow the same arrangement of hydrogel arrays to form various microfluidic routing and compartmentalization networks, simply by integrating microfluidic layers with different architectures. For example, as shown in FIG. 2*g*, an arrangement of six hydrogels may gate microfluidic networks with serial, parallel, and tree-like architectures (for exemplary visualization purposes, a blue dye may be embedded within the channels and the hydrogels are externally or locally heated).

Exemplary active epidermal biofluid harvesting from pressure-driven sources will now be described. An exemplary valving operation may actively sample, route, and compartmentalize epidermally retrievable biofluids from pressure-driven sources, pressure release mechanisms. Specifically, in the context of sweat as the target biofluid, a pressure release mechanism may avoid excess pressure build-up from the sweat glands. Without such mechanism in place, valve breakage may occur, due to the high pressure caused by accumulated sweat (as high as −500 mmHg with an air-tight sealed interface). An exemplary electrical circuit-hydraulic analogy shown in FIG. 3*a* involves a sweat gland characterized by a current source 302 (delivering current level Is) and a thermos-responsive valve characterized by a transistor switch 304. Here, the minimum turn-on voltage for the transistor switch may be denoted as $V_{min}$ and its maximum tolerable voltage may be denoted as $V_{max}$ (corresponding to its breakdown voltage). When directly connecting the transistor (in its off mode) to the current source, the built-up high voltage difference across the transistor (V) inevitably leads to transistor breakdown ($>V_{max}$). Similarly, as shown in the left side of FIG. 3*b*, when directly interfacing the air-tight closed valve ("microfluidic transistor switch") with actively secreting sweat glands (with secretion rate Qs), the built-up high pressure difference (P) across the valve inevitably leads, in this nonlimiting example, to the valve breakage ($P>P_{max}$, where $P_{max}$ denotes the valve's maximum tolerable pressure).

Figures 3A, 3B, 3C:
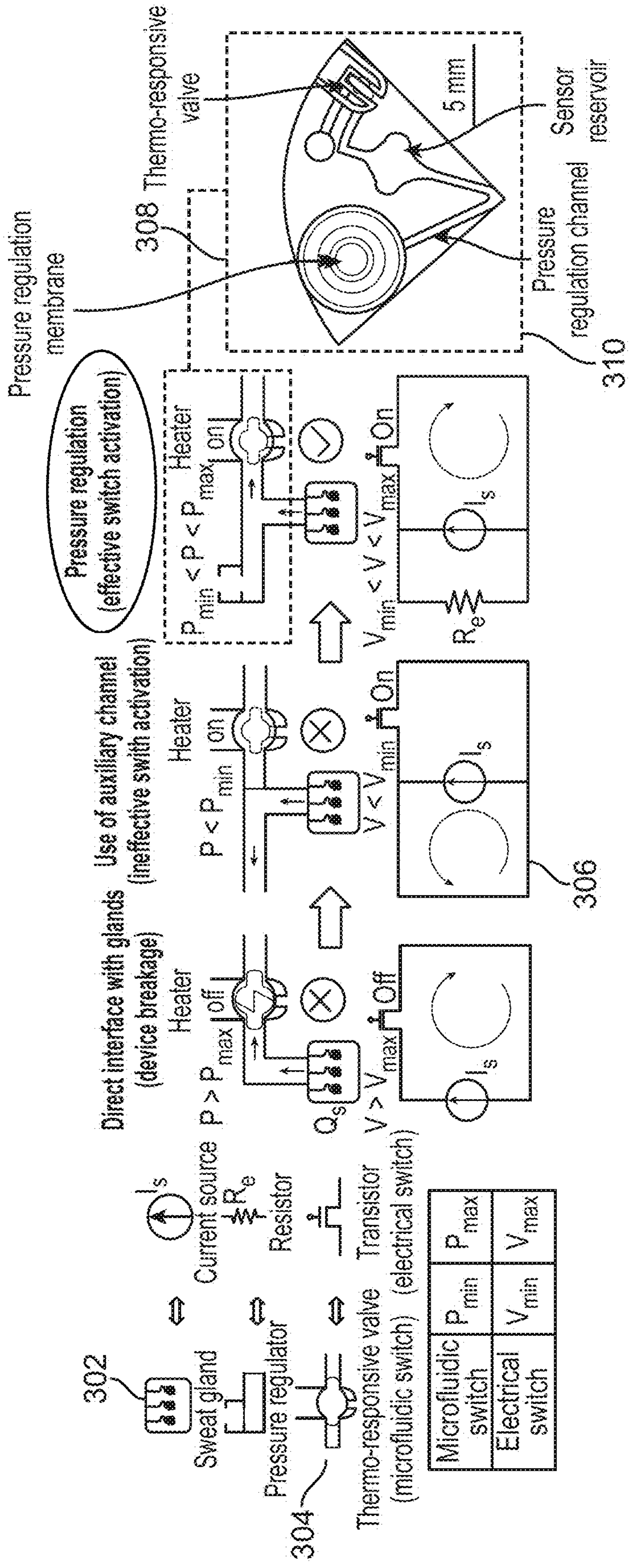
FIGS. 3*a*-3*h* illustrates exemplary elaboration, characterization, and demonstration of pressure regulated-valving.

In both exemplary scenarios, the addition of a secondary parallel electric/hydraulic conductive path 306 allows for redirecting the electrical current/fluid flow as a relief mechanism as shown in the center portion of FIG. 3*b*. However, it may be advantageous to tune electric/hydraulic resistance of these paths to ensure that the voltage/pressure across the respective switches may be maintained above $V_{min}/P_{min}$ (where switches may be turned on). Electrically, this can be achieved by adding a parallel resistor ($R_e$). Hydraulically, exemplary implementations may include a membrane filter 308 incorporated within an auxiliary microfluidic channel 310 to render the desired hydraulic resistance, which effectively serves as a pressure regulation mechanism as shown in FIG. 3*c*.

Figures 3D, 3E, 3F, 3G:
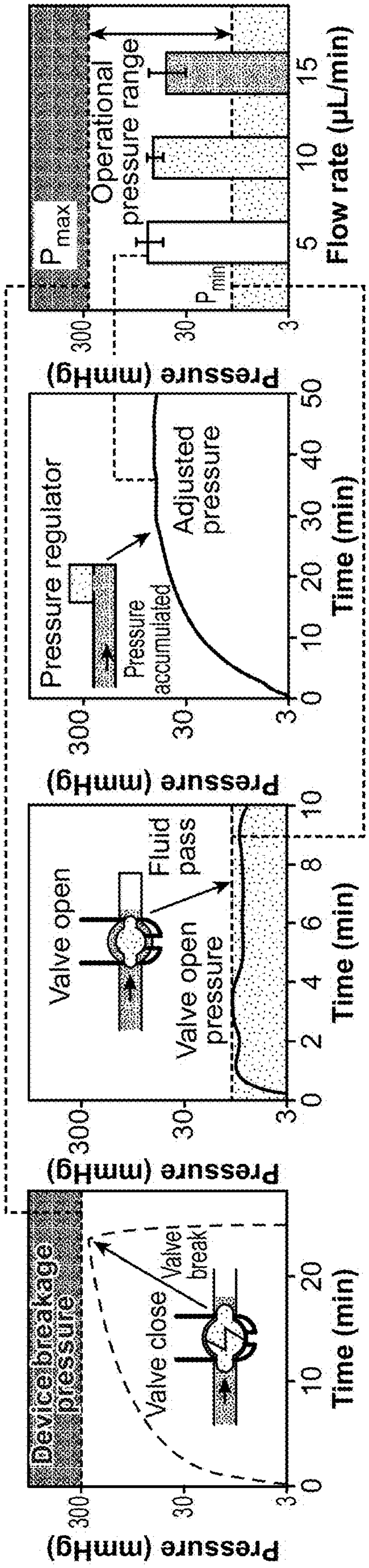
Figure 3H:
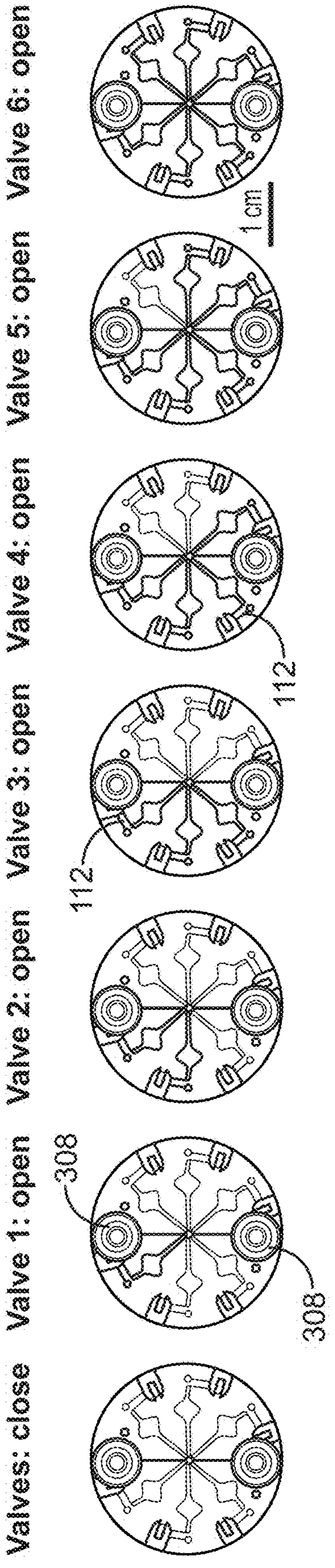
Figure 13:
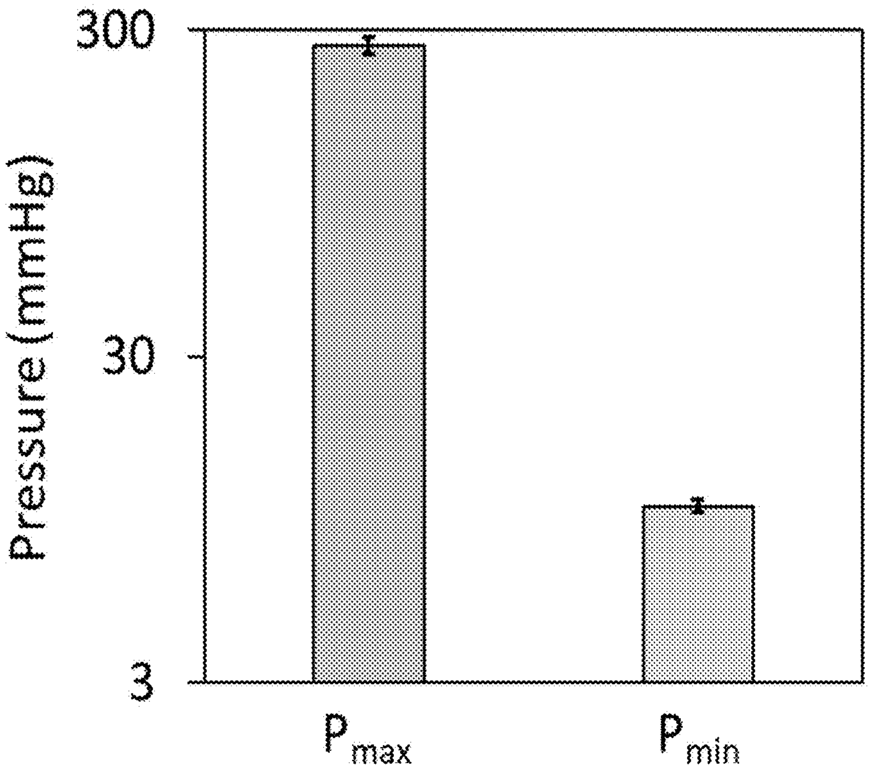
FIG. 13 illustrates an exemplary characterization of a maximum tolerable pressure ($P_{max}$) and minimum required pressure ($P_{min}$). Exemplary error bars indicate standard error (n=3).

To characterize $P_{max}$ and $P_{min}$ for an exemplary pressure regulated valving interface, the same test setup as that of FIG. 2*c* may be used (with a programmed input flow rate of 5 L/min). As shown in FIG. 3*d*, the direct injection of fluid through the closed-valve microfluidic device (using a syringe pump) may result in pressure built-up on the order of 300 mmHg (corresponding to $P_{max}$), beyond which the device failed (due to leakage), as evident from the annotated drop in the measured pressure. Furthermore, as shown in FIG. 3*e*, the injection of fluid through the opened-valve microfluidic device may results in approximately 10 mmHg pressure (corresponding to $P_{min}$) across the device. Characterization of an exemplary microfluidic pathway, with the pressure regulation mechanism in place as shown in FIG. 3*f*, illustrates the mechanism's ability to effectively maintain the operational pressure (P) within the permissible pressure range ($P_{min}<P<P_{max}$) for different input flow rates as shown in FIG. 3*g* (see also FIG. 13). In addition, FIG. 3*h* shows that a fully formed valving system (consisting of heater-coupled hydrogel valves 112 and pressure regulating implementations 308) can be successfully used to route and compartmentalize fluid (e.g. biofluid) in an addressable and electronically programmable manner.

Figure 4A:
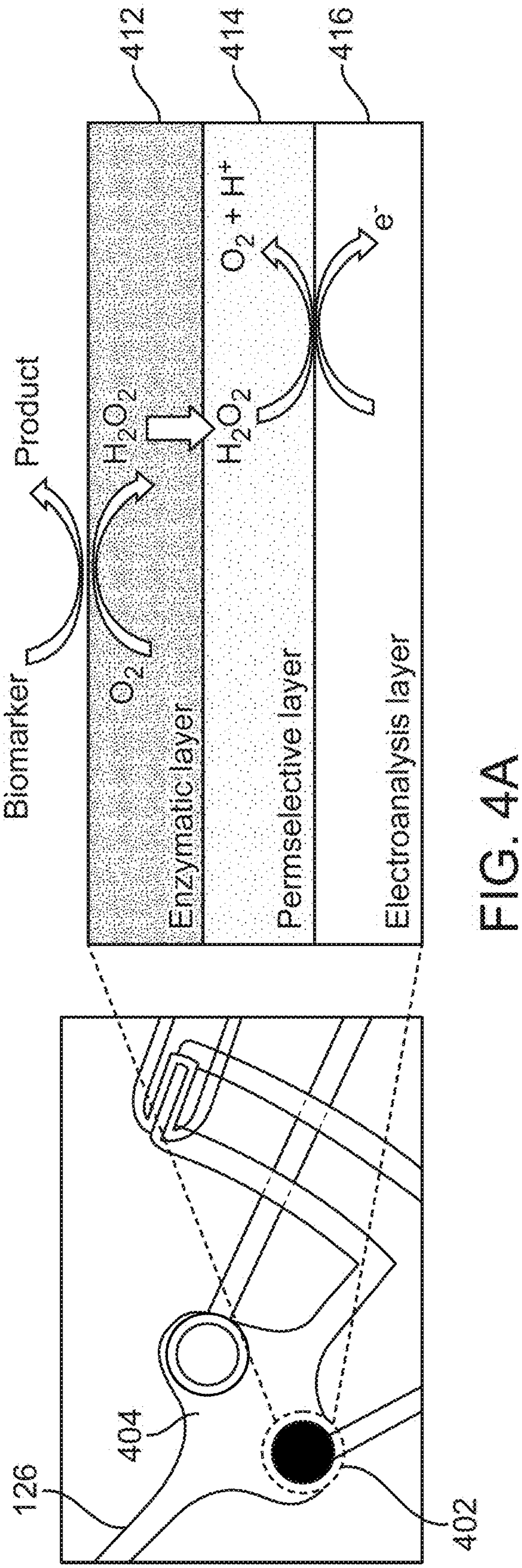
FIGS. 4*a*-4*g* illustrate an exemplary flow rate-undistorted biomarker analysis.
Figure 4C:
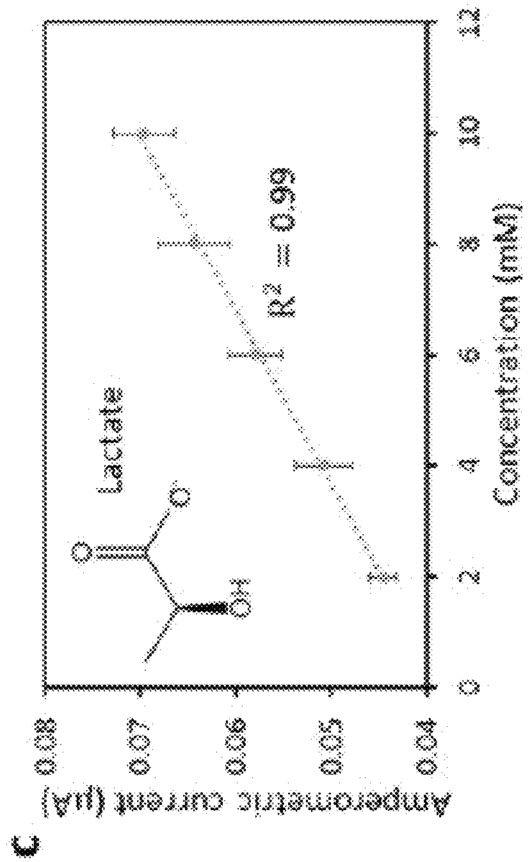
Figure 4B:
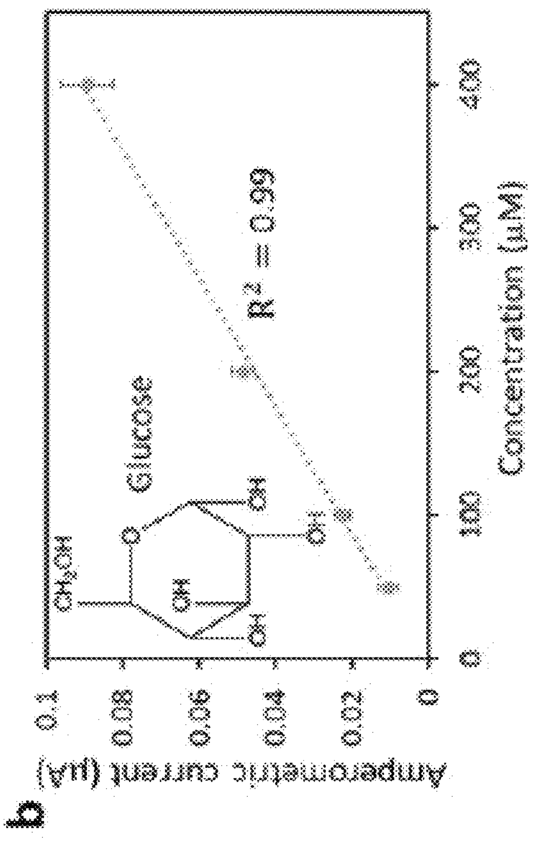

An exemplary application of microfluidic valving for flow rate-undistorted biomarker analysis will now be described. In some implementations, an active biofluid management system may include biochemical sensing interfaces 402 incorporated in the sensing chamber or reservoir 404 of the valve-gated compartments for holding biofluids permitted to flow by the valve (e.g. upstream of each compartment channel 126 as shown in FIG. 4*a*), in accordance with mediator-free enzymatic sensor development methodology. Exemplary sensing interfaces may target glucose and lactate as examples of informative metabolites. As illustrated in FIG. 4*a*, exemplary corresponding sensing interfaces may include 1) an enzymatic layer 412 (e.g. glucose oxidase or lactate oxidase) to catalyze oxidation of target molecules and generate hydrogen peroxide ($H_2O_2$) as a detectable byproduct; 2) a permselective membrane 414 (e.g. poly-m-phenylenediamine) to reject interfering electroactive species; and 3) an electroanalysis layer 416 (e.g. platinum) to detect the generated $H_2O_2$. The response of the glucose and lactate sensors may be validated within the respective analytes' physiologically relevant concentration range in sweat. As shown in FIGS. 4*b* and 4*c*, for both sensors, substantially linear relationships may be observed between the measured current responses and target analytes' concentration levels ($R^2=0.99$, for both sensors).

An exemplary active biofluid flow control achieved by the valving system of embodiments can be leveraged to address sensor-level challenges relevant to wearable biomarker sensing. In some implementations, the valving capability may decouple a confounding influence of flow rate variability on sensor response. In a generalizable continuous microfluidic electrochemical sensing setting, an exemplary response of the sensor may be flow rate-dependent, because of the central role of advective flow in transporting analytes to the sensor. In the case of electrochemical sensing, the sensor current response (I) may be proportional to the flux of analyte molecules onto the sensor surface, which in turn may be directly proportional to the local concentration gradient $$\left(M = \frac{\delta_c}{\delta_z}\right).$$

In that regard, determining the local concentration gradient may include the consideration of various coupled phenomena, including advective and diffusive analyte transport to the sensor surface, and the reaction rate at the sensor surface. Exemplary implementations may assume the sensor has a high surface reaction rate, and that advection may be the dominant form of analyte transport (manifested as Peclet number>>1, due to the relatively high sweat rate Q~1-10 μL/min during active secretion). The exemplary analysis based on these assumptions leads to the $I \propto M \propto \sqrt[3]{Q}$ relationship.

Figure 4D:
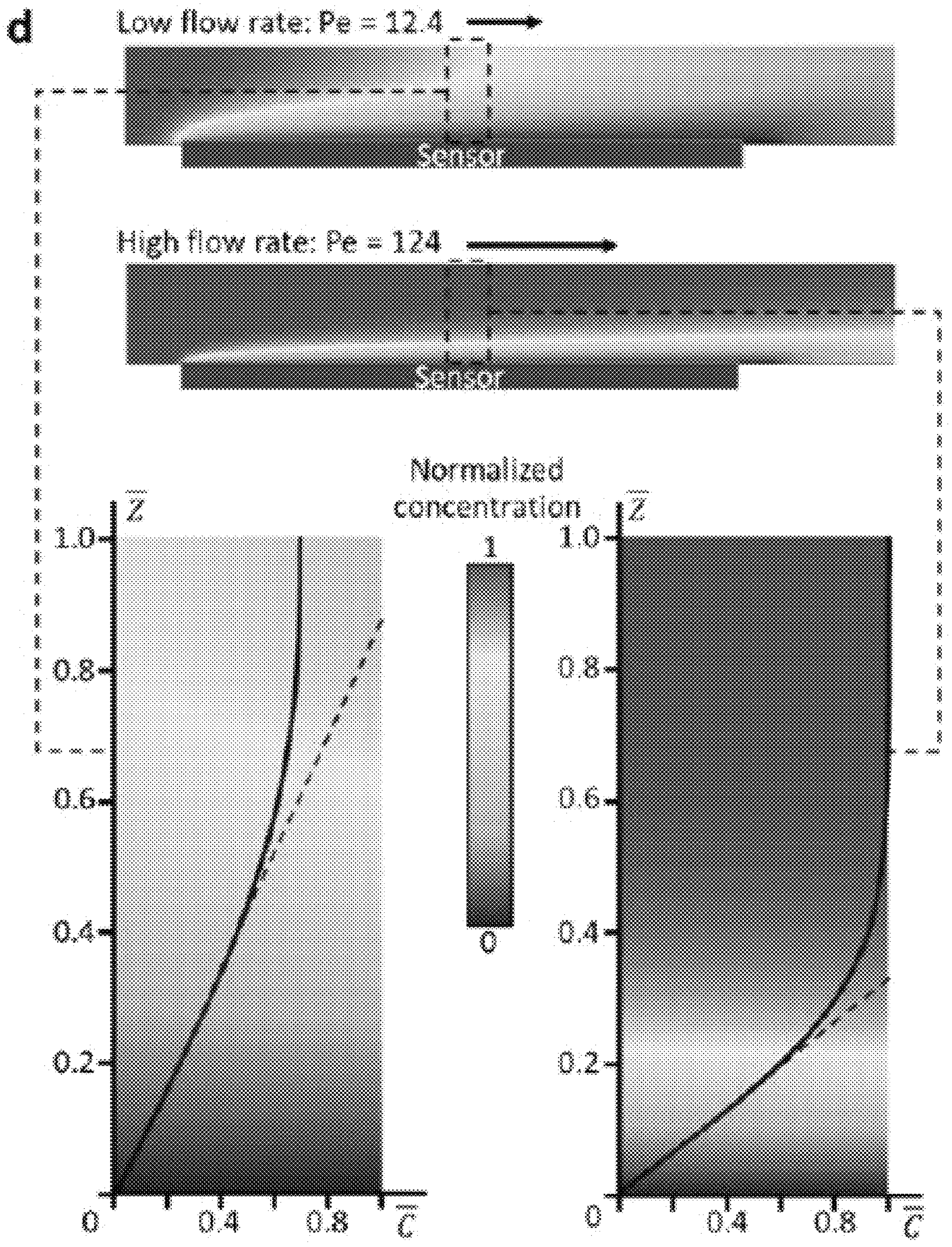
Figure 4E:
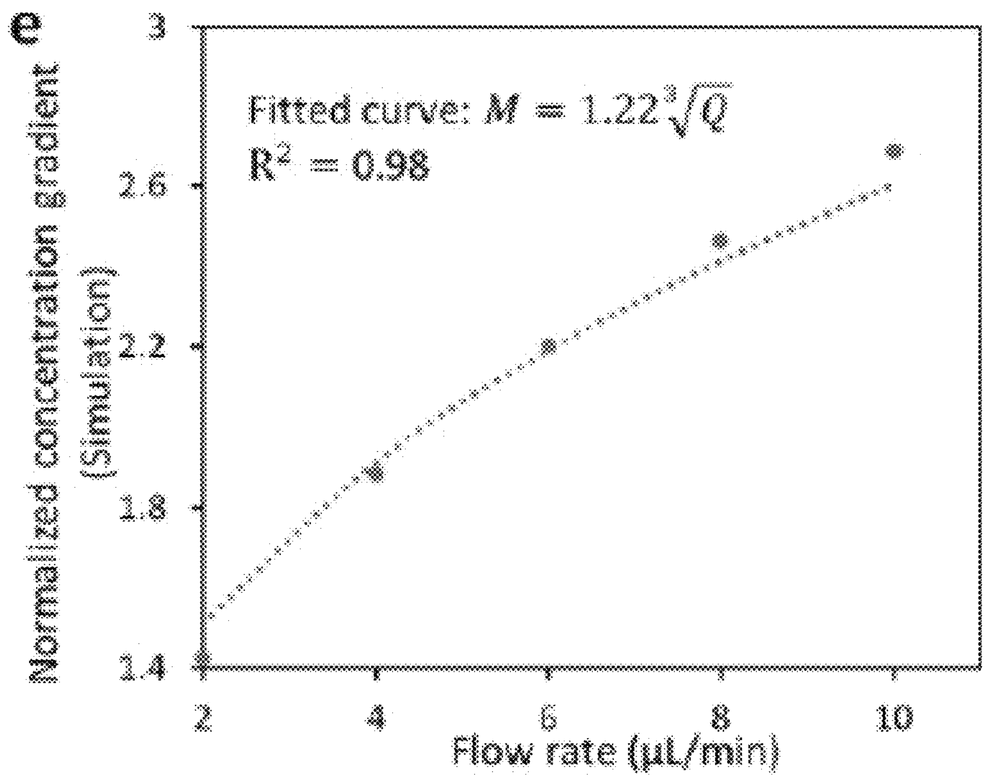
Figure 4F:
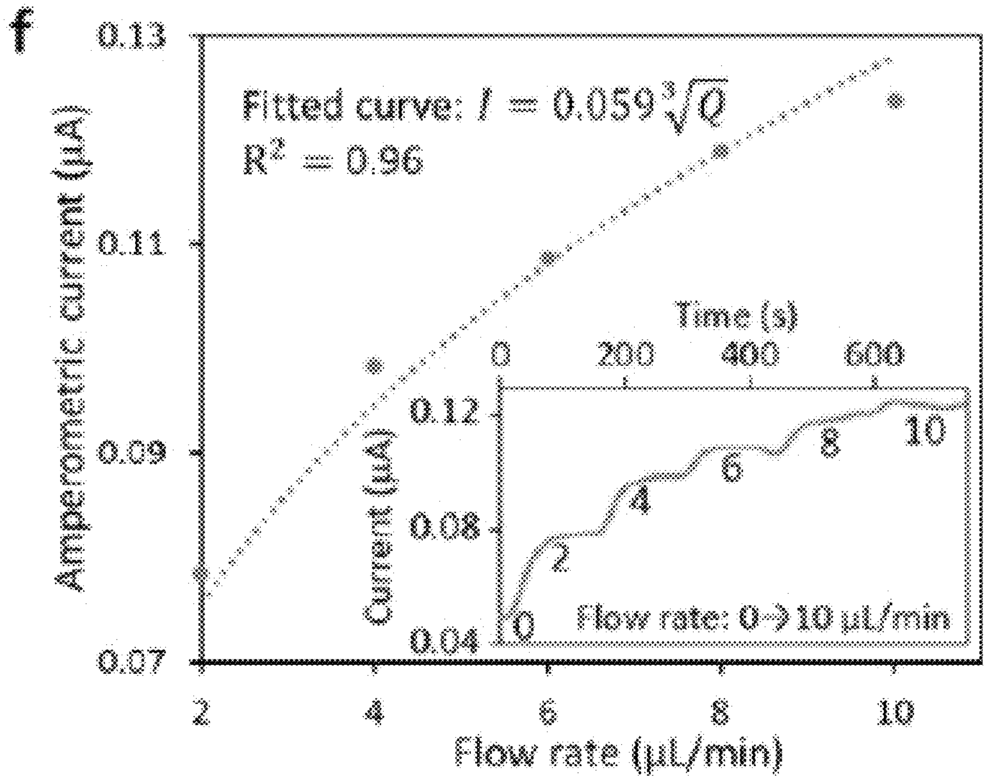

This relationship may be validated through finite element analysis (e.g. COMSOL), by simulating an exemplary analyte concentration profile at the sensor surface in response to various continuous flow rates (within the physiologically relevant range of sweat secretion rate). As shown in FIGS. 4*d* and 4*e*, an exemplary concentration gradient on the sensor surface may increase along with the flow rate in the microfluidic chamber, in which M may be proportional to $\sqrt[2]{Q}$($R^2$=0.98).
Similarly, as shown in FIG. 4*f*, an exemplary measured amperometric current of a representative glucose sensor presents a cube-root relationship with Q ($R^2$=0.96).

Figure 4G:
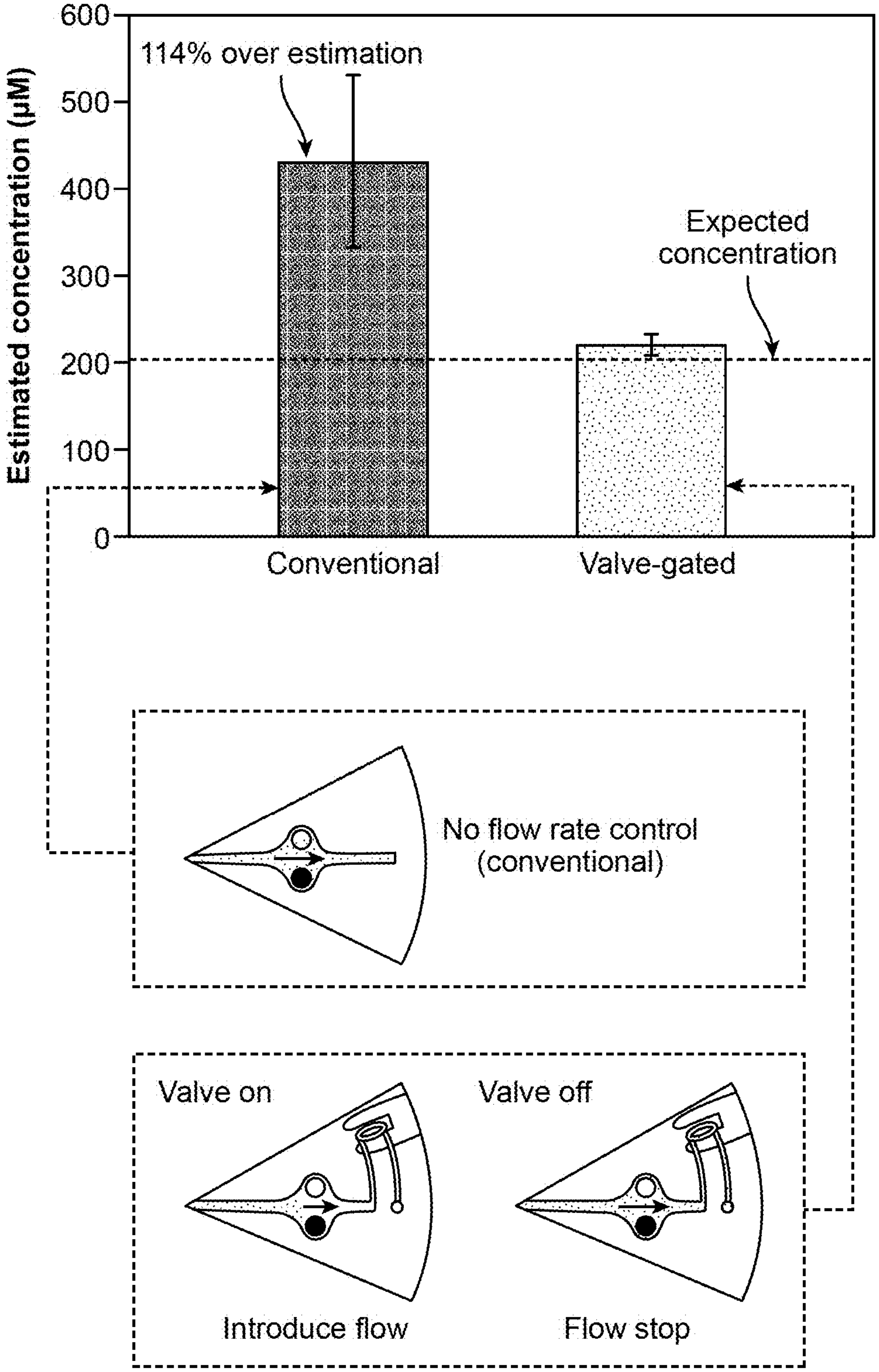

Without accommodating for the influence of dynamically varying flow rate (during on-body measurements), if various calibration methods are followed (which may be performed at zero flow rate, ex-situ), risk of inaccurate biomarker measurements may increase. An exemplary valving mechanism allows for performing analysis in a sample-and-hold manner. In some implementations, in a valve-gated sensing chamber, the valve can be opened, to allow for the introduction of the sample into the sensing chamber, and closed, to allow for sample compartmentalization and sensing at zero flow rate, thus effectively decoupling the confounding influence of flow rate variability. An exemplary response of a representative glucose sensor to an introduced sample (containing 200 μM glucose) may be monitored at 5 μL/min (no valve) and 0 μL/min (corresponding to valve-gated condition), and the corresponding estimated concentrations may be derived by referring to the calibration curve (obtained at 0 μL/min). As shown in FIG. 4*g*, a conventional setup may overestimate the glucose concentration by 114%, whereas the exemplary valve-gated condition accurately estimated the glucose concentration.

Figure 5A:
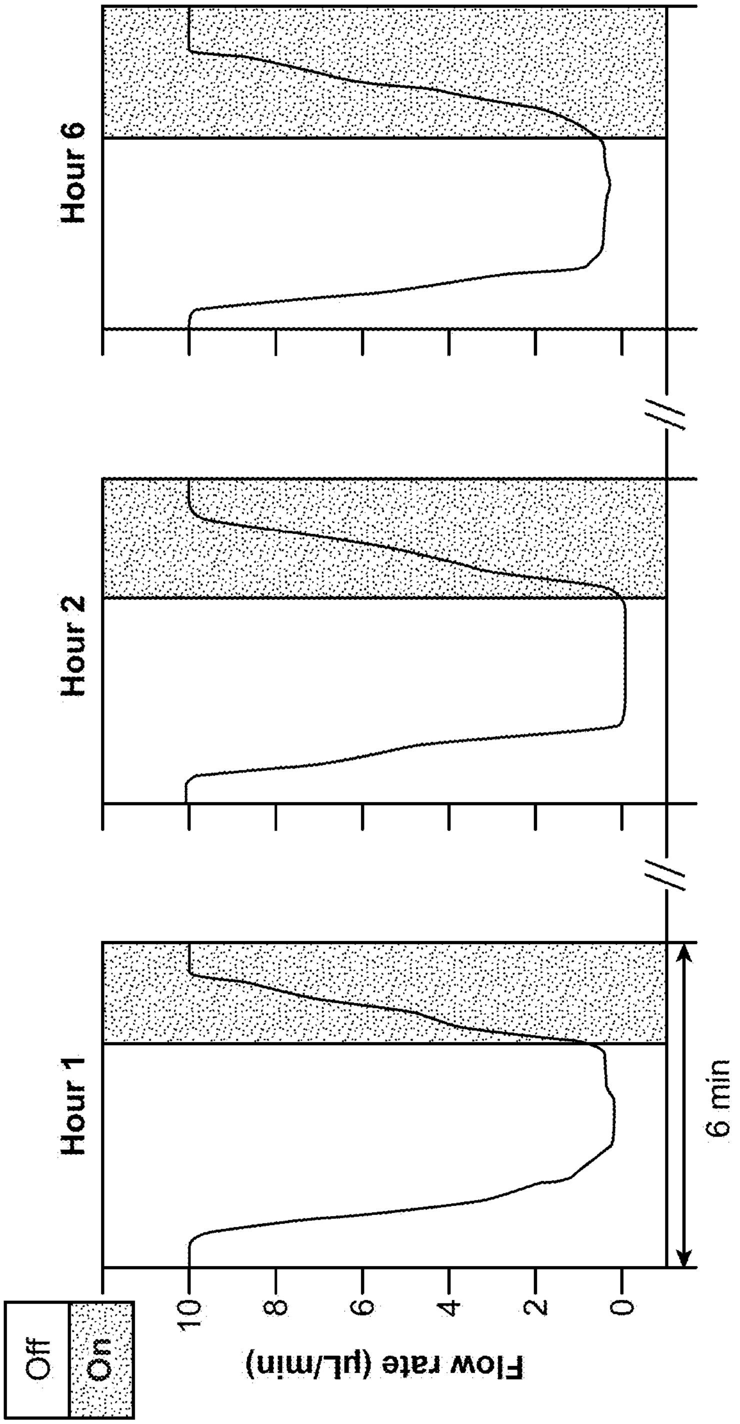
FIGS. 5*a*-5*f* illustrates exemplary integration and characterization for contextually-relevant on-body biomarker analysis.
Figure 5B:
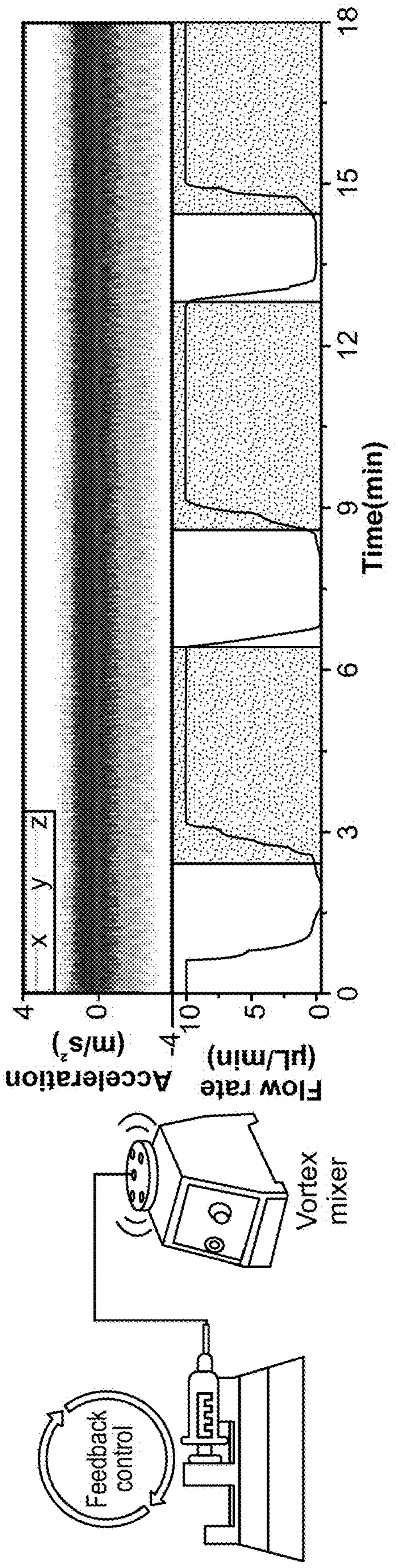
Figure 14:
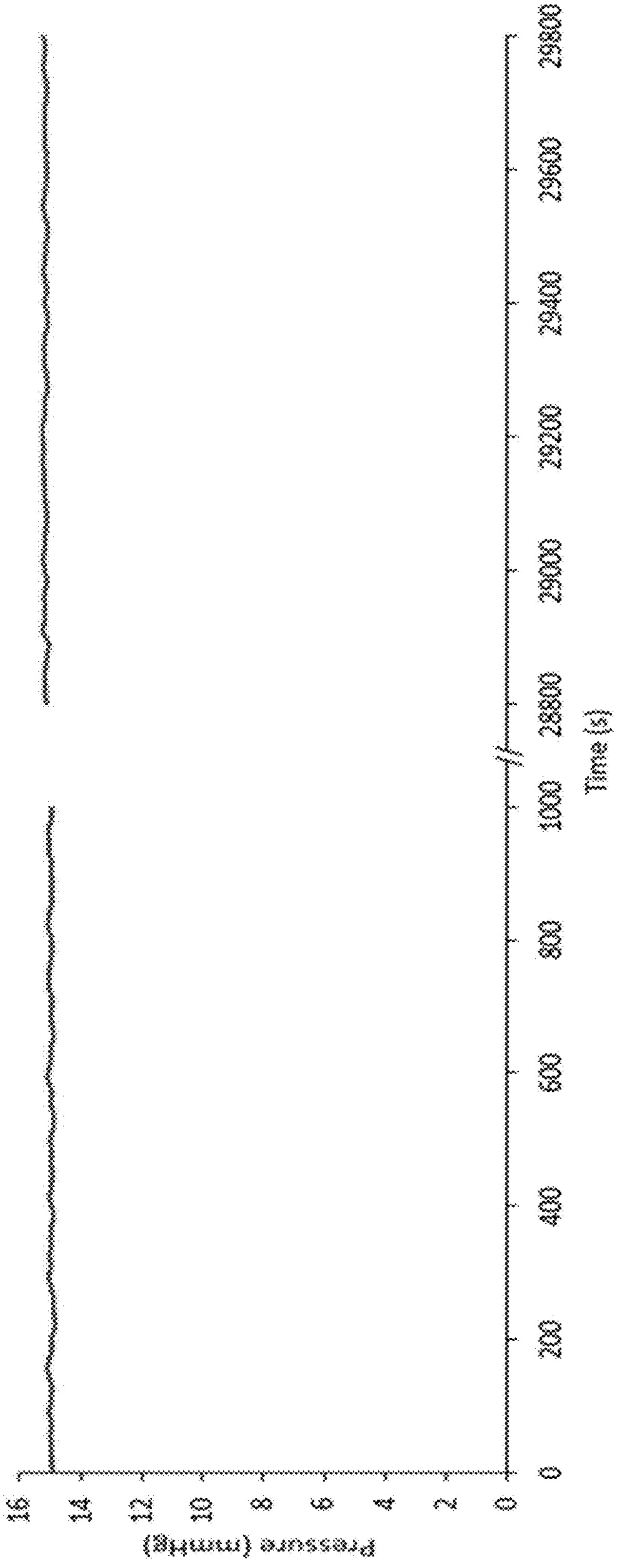
FIG. 14 illustrates an exemplary validation of prolonged valve sealing. Maintenance of constant pressure across an exemplary valve-gated channel indicates that a channel can remain fully sealed by an exemplary embedded hydrogel without suffering from possible dehydration-induced shrinkage effects. Exemplary pressure characterization occurs over 8 h, and exemplary pressure data spans the first and last 1000 s-period of exemplary window to illustrate the unchanged sealing status.
Figure 15:
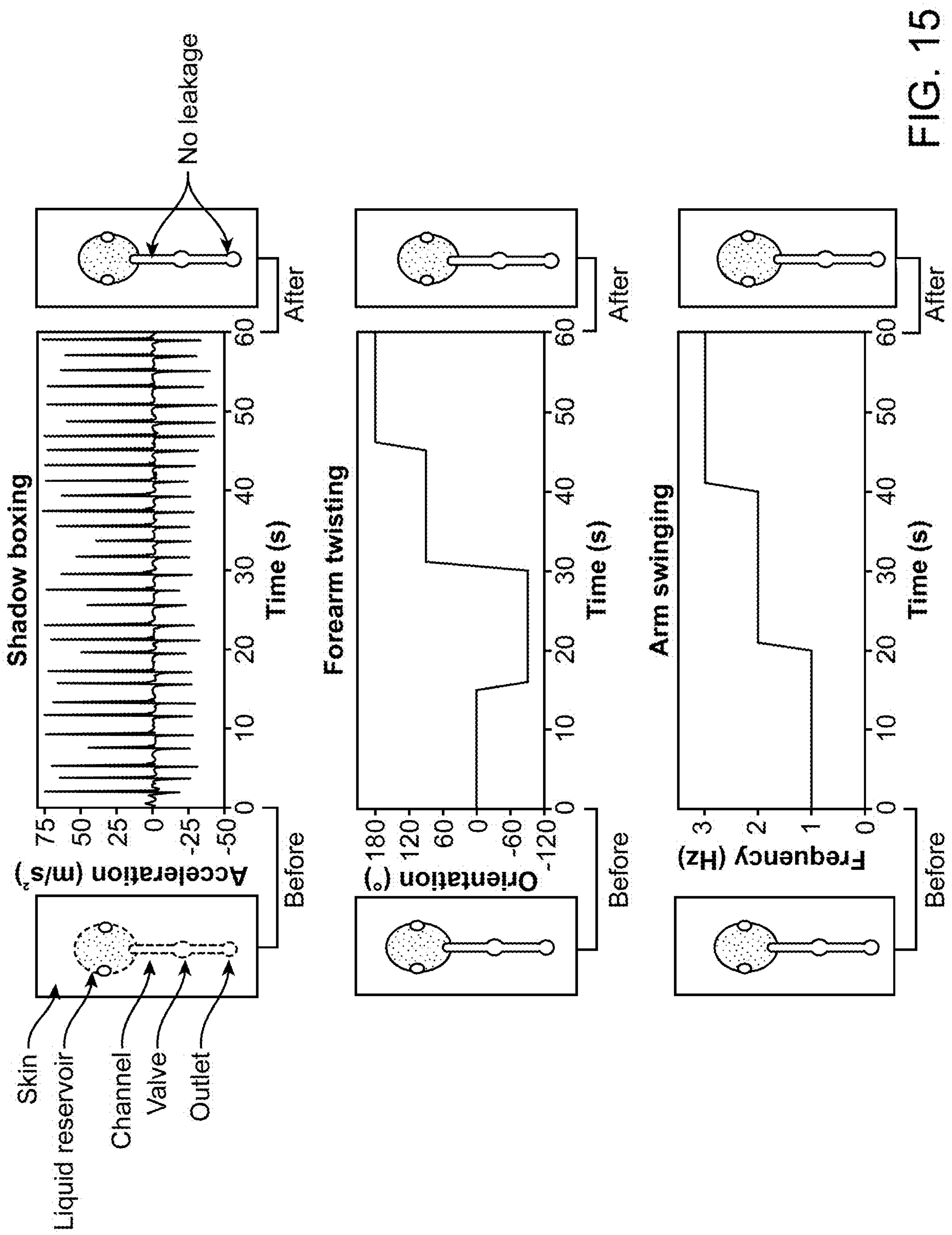
FIG. 15 illustrates exemplary on-body validation of valve sealing with a subject wearing the microfluidic module on the forearm and performing shadow boxing (top), forearm twisting (middle), and arm swinging (bottom) at different acceleration levels, orientations, and frequencies, respectively. Optical images of an exemplary microfluidic module before/after the activities demonstrate leakage-free preservation of an exemplary compartmentalized blue-dyed sample, illustrating the device robustness under routine user motion.
Figures 16A, 16B, 16C, 16D:
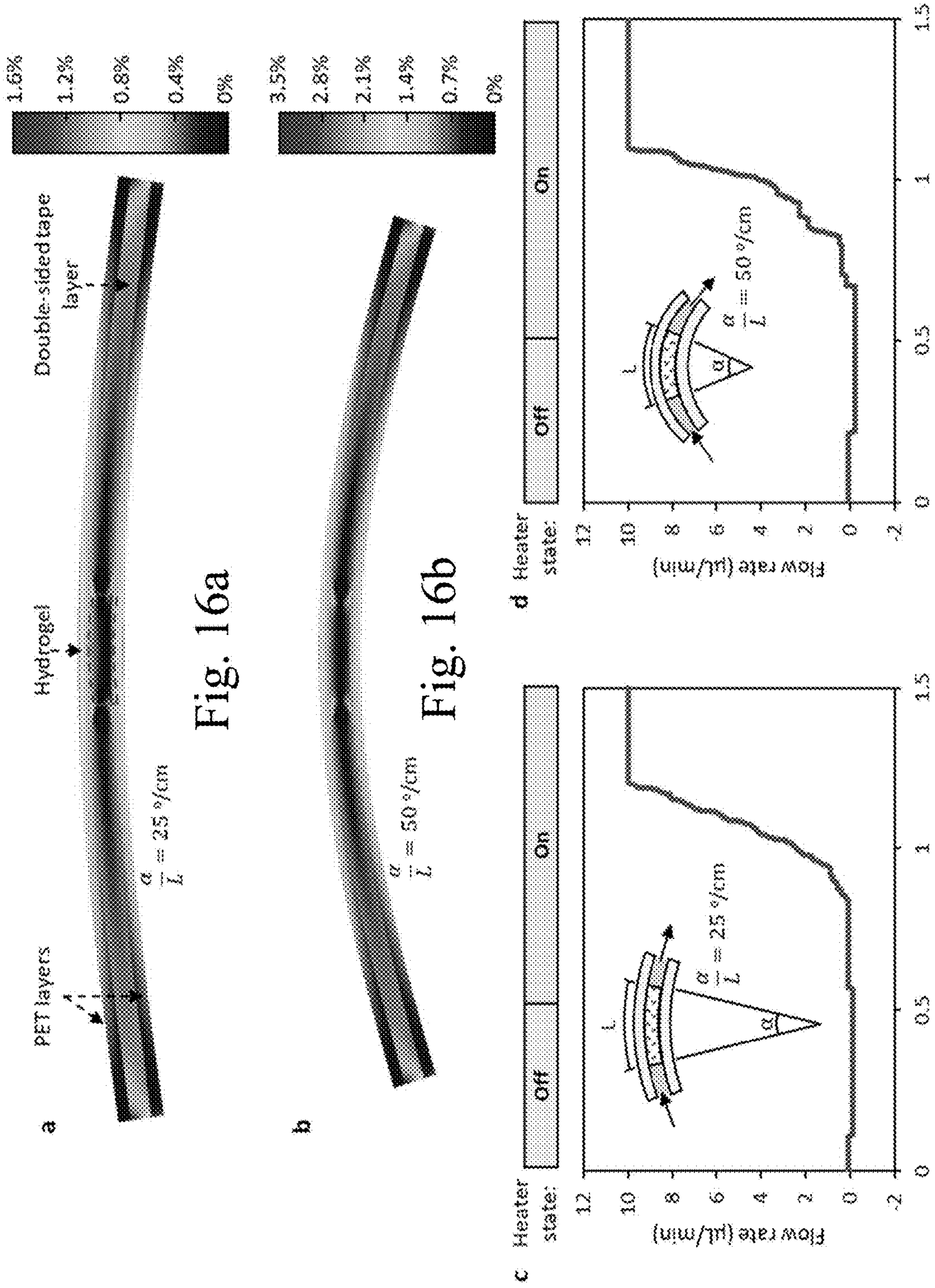
FIGS. 16*a*-16*b* illustrate an exemplary COMSOL-simulated strain profile (cross-view) of a flexible microfluidic valve, under two different exemplary device bending curvatures: a α/L=25 o/cm and b α/L=50 o/cm. An exemplary hydrogel sustains minimal strain, as it is located at the neutral plane. Exemplary device characteristics include, but are not limited, to: Hydrogel valve: 1 mm in length, 170 m in height.
FIGS. 16*c*-16*d* illustrate experimental validation of fluid valving under two device bending curvatures: c α/L=25 o/cm and d α/L=50 o/cm. An exemplary valve is activated after 0.5 min.
Figure 17A:
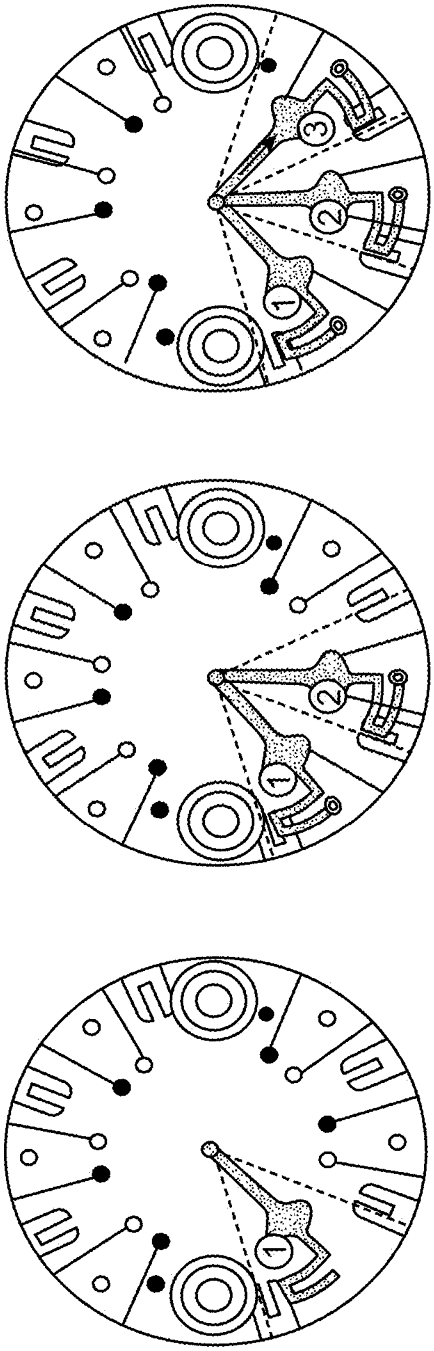
FIG. 17*a* illustrates an exemplary intermittent sample compartmentalization via sequential on-body valving (using blue dyes for visualization).
Figure 17A:
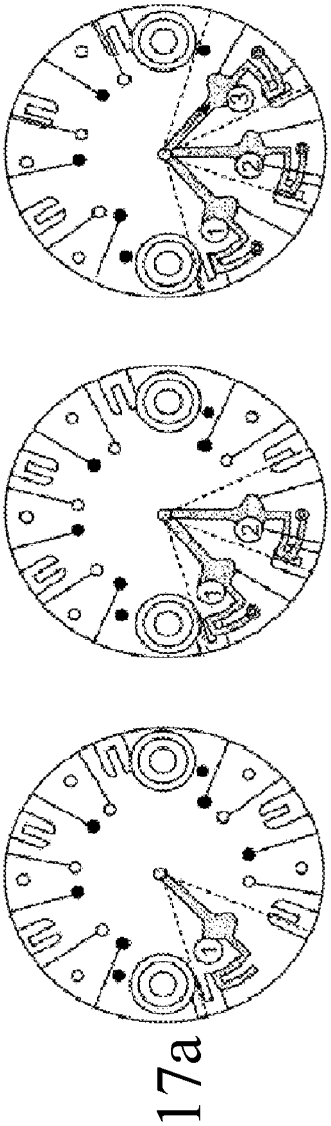
Figure 17B:
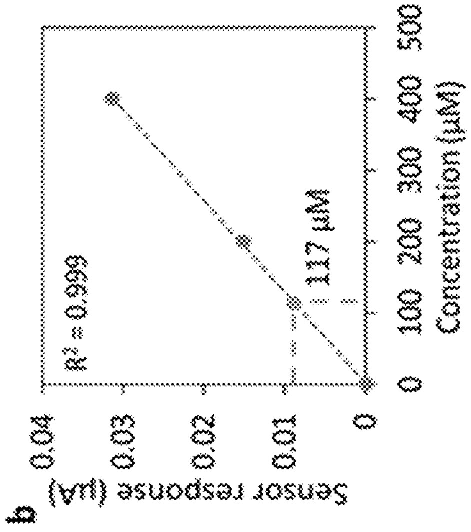
FIGS. 17*b*-17*d* illustrate exemplary on-body sweat glucose (b, c) and lactate (d) sensor readouts and corresponding exemplary calibration curves. Exemplary sweat glucose readouts in (b) and (c) are obtained before and after beverage intake, respectively.
Figure 17C:
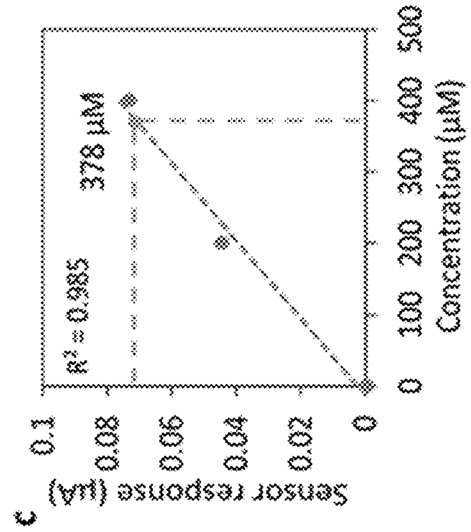
Figure 17D:
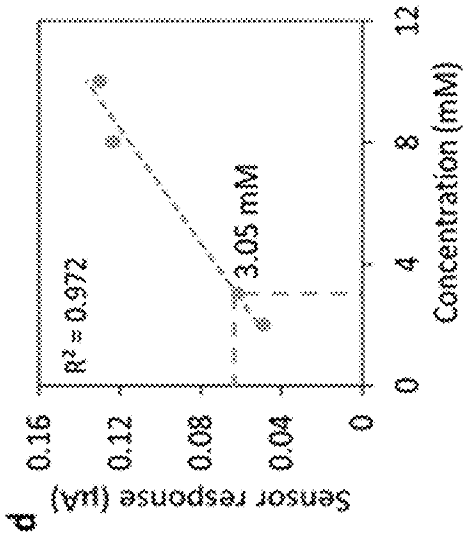

Exemplary integration and characterization for contextually-relevant on-body biomarker analysis will now be described. An exemplary pressure-regulated valving system for on-body biofluid management and biomarker analysis may possess operational stability during prolonged use and in the presence of motion artifacts. An exemplary flow rate characterization setup (e.g., the same as that used in FIG. 2*c*) may quantitatively monitor the performance of a pressure-regulated valve in an ex-situ setting. First, to assess its stability during a prolonged testing period, an exemplary implementation may sequentially activate and deactivate the valve at set timepoints over a period of 6 hours. FIG. 5*a* shows that an exemplary flow rate, injected by pressure-driven syringe pump, may successfully be reduced to zero and back to its default value upon deactivation and activation of the valve, respectively. Additionally, FIG. 14 illustrates that an exemplary hydrogel dehydration does not affect valving operation, as evident from maintenance of a relatively constant exemplary pressure-across a valve-gated channel-over an exemplary amount of time of 8 hours. The minimal impact of hydrogel dehydration can be attributed to the small size of the outlets, minimizing the evaporation rate in this example. Furthermore, to evaluate the stability of the exemplary valving system against motion artifacts, its performance may be characterized under oscillatory motion (amplitude: ~3 $m/s^2$ at 5 Hz, generated by a vortex mixer). An exemplary measured flow rate profile, shown in FIG. 5*b*, indicates the successful opening and closing of the valve. Exemplary ex-situ and in-situ characterizations of FIGS. 15 and 16 illustrate robustness of an exemplary valving interface in the presence of mechanical deformation and unconstrained body motion. Altogether, exemplary ex-situ characterization illustrates the preserved functionality of the valve over the test periods/conditions, informing the robustness of the valving operation for on-body application.

Figure 9A:
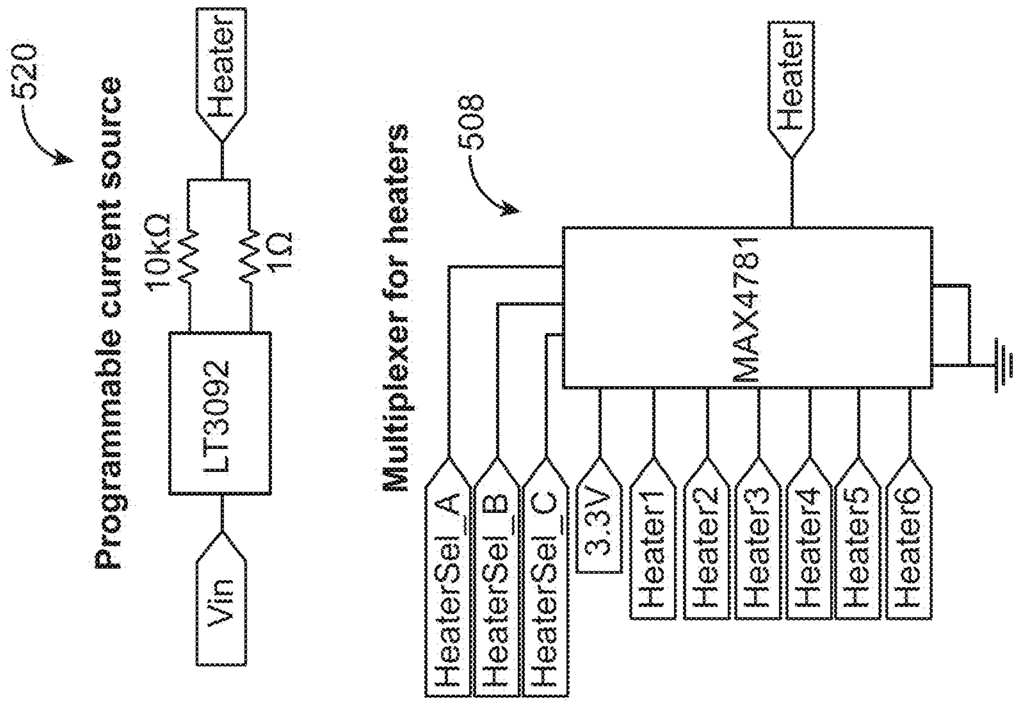
FIG. 9*a* is a schematic diagram illustrating an exemplary actuation circuit, including a programmable current source and multiplexer (for microheaters) circuitries.
Figure 9B:
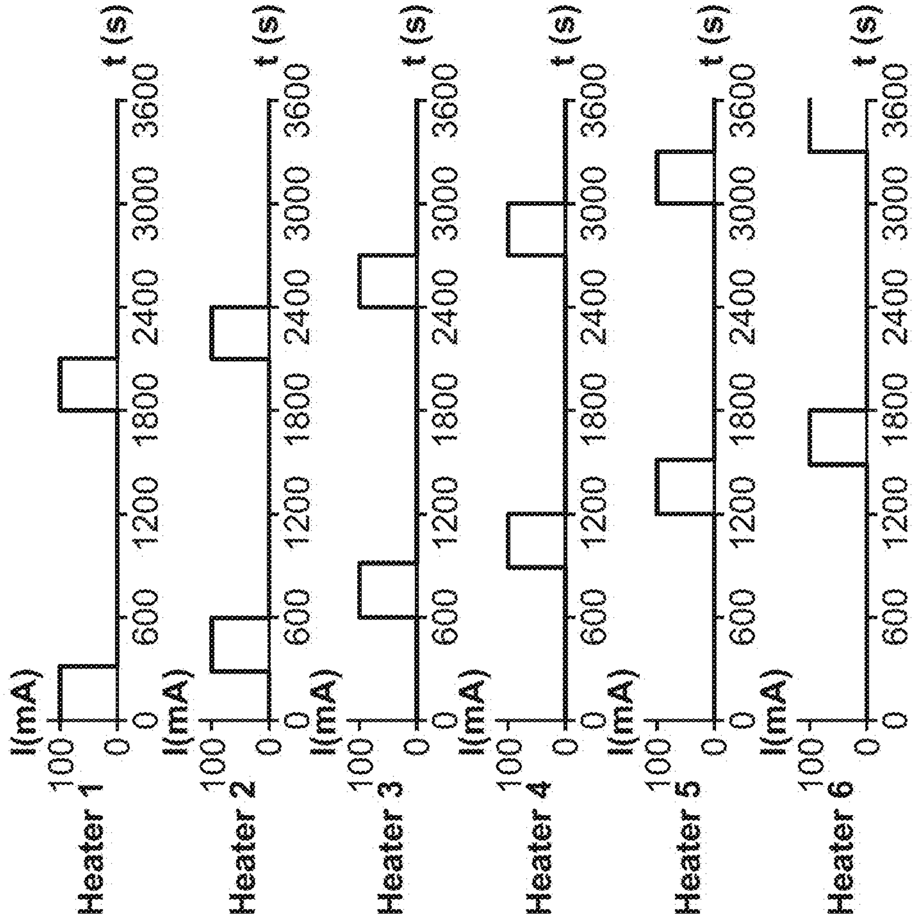
FIG. 9*b* illustrates exemplary measured current through six electrical resistive microheaters upon the periodic and sequential activation and deactivation of the exemplary microheater array (resistive load may be, by way of example, 25Ω, connected at the output of each of the actuation channels).
Figure 10:
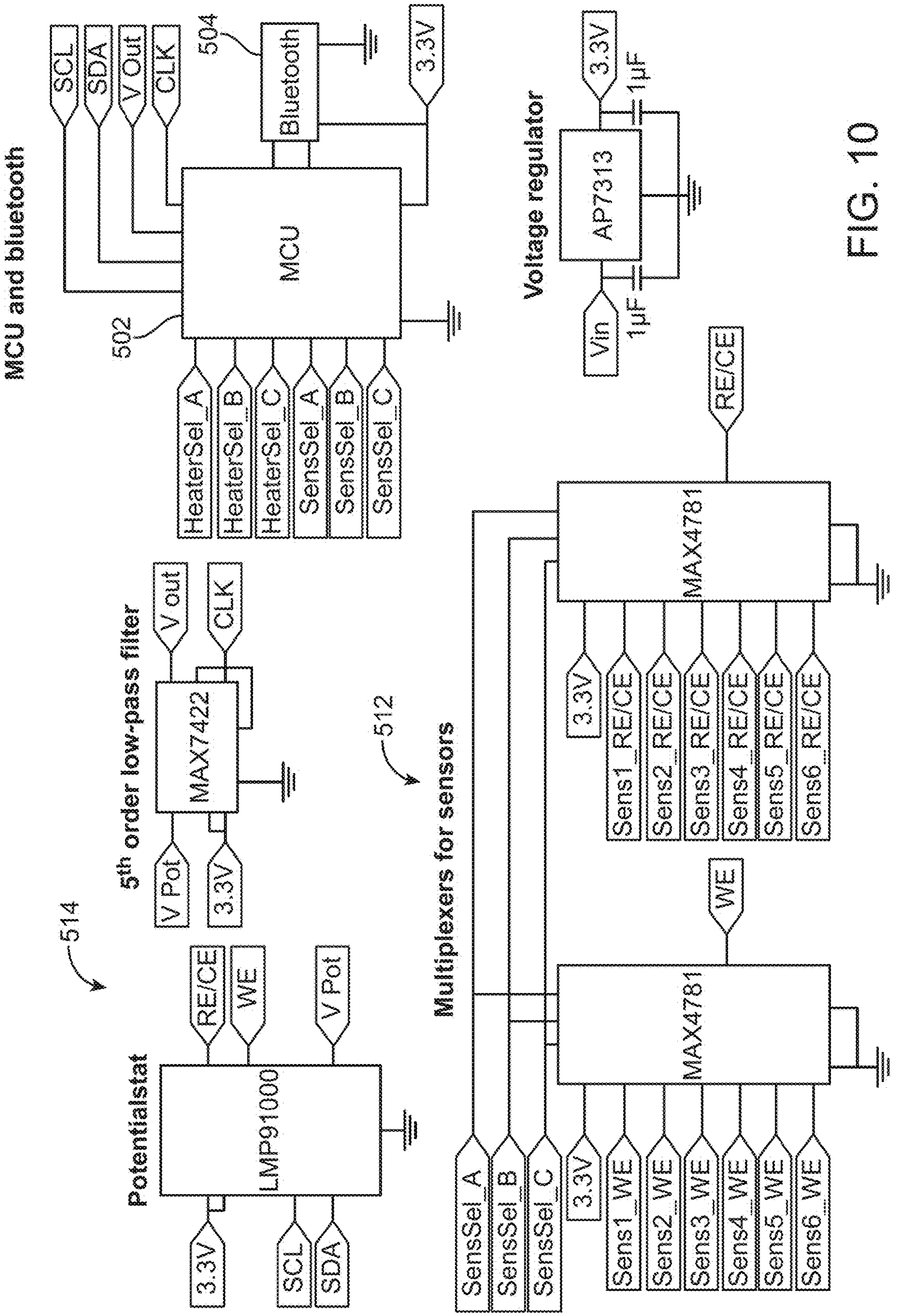
FIG. 10 are schematic diagrams illustrating exemplary implementations for sensing (including potentiostat and lowpass filter (LPF)), microcontroller unit (MCU), wireless transmission (Bluetooth®), and power regulating circuits.

To realize a wearable valve-enabled bioanalytical platform with seamless control command and biomarker data communication capabilities, an exemplary sensor array-coupled valving system may be interfaced with a custom-developed wireless FPCB (example schematic diagrams of which are shown in FIGS. 9 and 10). Structurally, an exemplary FPCB module is 100 μm-thick, and its base material is polyimide, the Young's modulus of which is on the same order as those of the materials used in the microfluidic module's structure (see Table 1 below). In case a higher degree of mechanical flexibility is needed (e.g., when interfacing high curvature areas), other base materials with lower Young's modulus can be used to construct a circuit board in accordance with present implementations. It should be noted that although described herein as a PCB, the module 104 may be implemented in many various ways known to those skilled in the art, including as a single device (e.g. an application specific integrated circuit (ASIC)), one or more interconnected integrated circuits, etc. It should also be appreciated that it is not necessary that all components of the FPCB described herein be co-located in one device, but can be arranged, separated and co-located in many various ways, including some or all components located in an associated smart device such as a smart phone.

TABLE 1

| Material | Young's Modulus |
|---|---|
| PET | 2.7 GPa |
| Hydrogel | 5 kPA |
| Polyimide | 2.5 GPa |

Figure 5C:
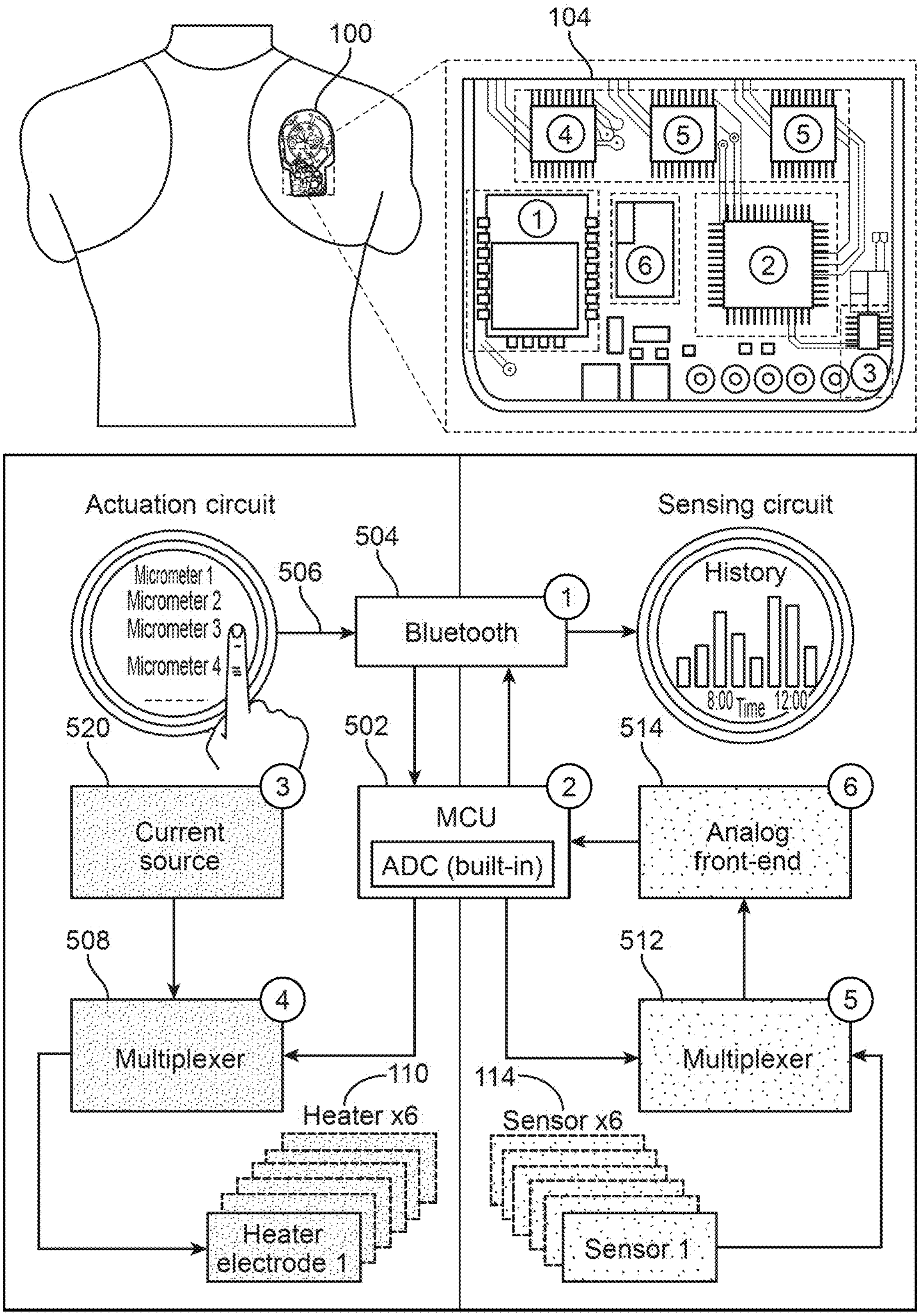

FIG. 5*c* illustrates an operational block diagram of the exemplary FPCB 104, which may be capable of rendering multi-channel valve-actuation and signal processing. Depending on the context at hand and the desired mode of analysis, an activation signal for the designated valve-gated sensing compartment may be transmitted to the FPCB's microcontroller unit (MCU) 502 (e.g. via a Bluetooth® wireless interface 504). This activation signal 506 can be generated through a scheduled timetable or on-demand (initiated by the user). Upon processing the received command, and with the aid of a multiplexer unit 508, the exemplary MCU selects the appropriate actuation channel to power the corresponding microheater 110 by a current source, subsequently opening the desired valve. Subsequently, the harvested biofluid may be routed to the selected compartment. Then, following MCU-generated instructions, the valve closes, and the sensor 114 response may be recorded and processed by an analog front-end (consisting of potentiostat and low-pass filter units) via the multiplexer 512-selected sensing channel. The signal processed by the analog front-end 514 may then be translated to digital at the MCU 502 level, and wirelessly communicated to a user interface (e.g. via a Bluetooth® wireless interface 504). An exemplary user interface can display the acquired biomarker information in real-time and to store it in the user's database.

Figure 5D:
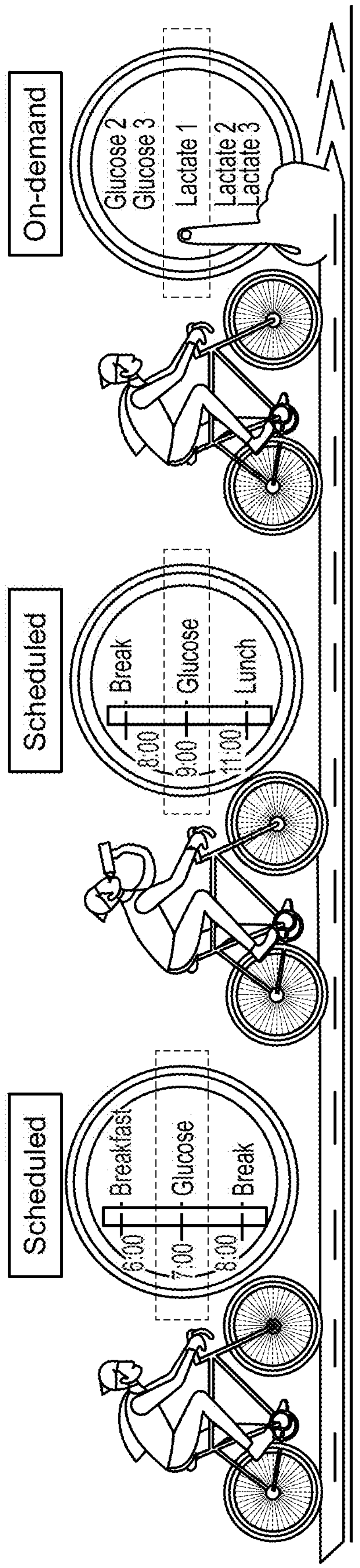
Figure 5E:
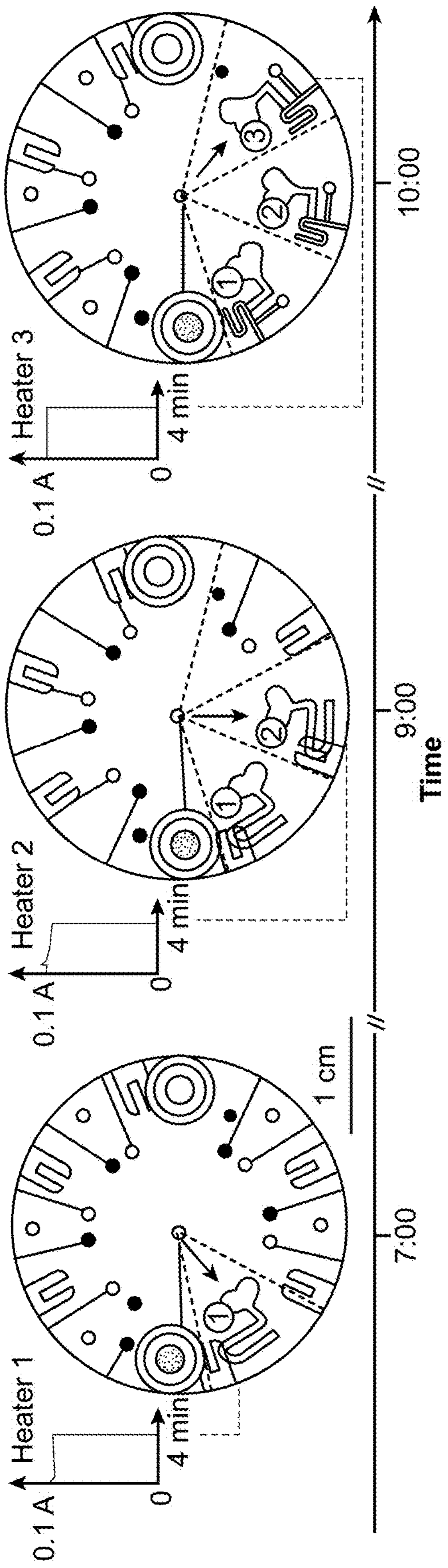
Figure 5F:
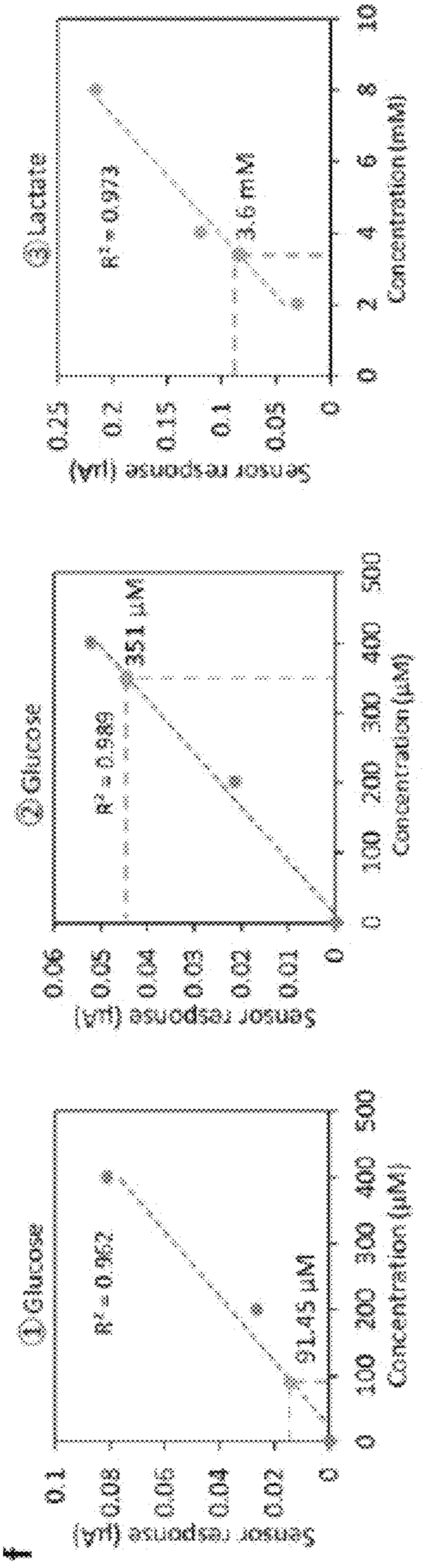
Figure 11A:
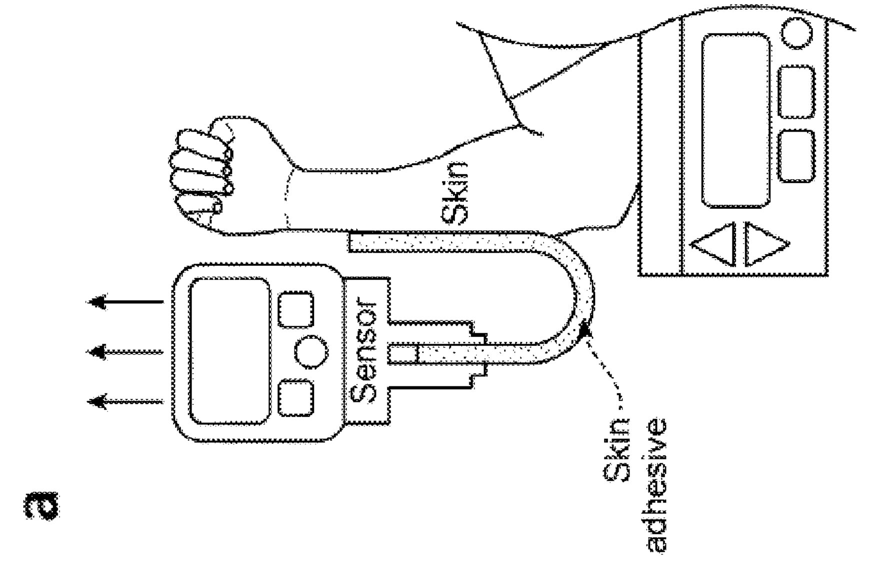
FIG. 11*a* illustrates an exemplary implementation for characterizing 180° peeling adhesion force.
Figure 11B:
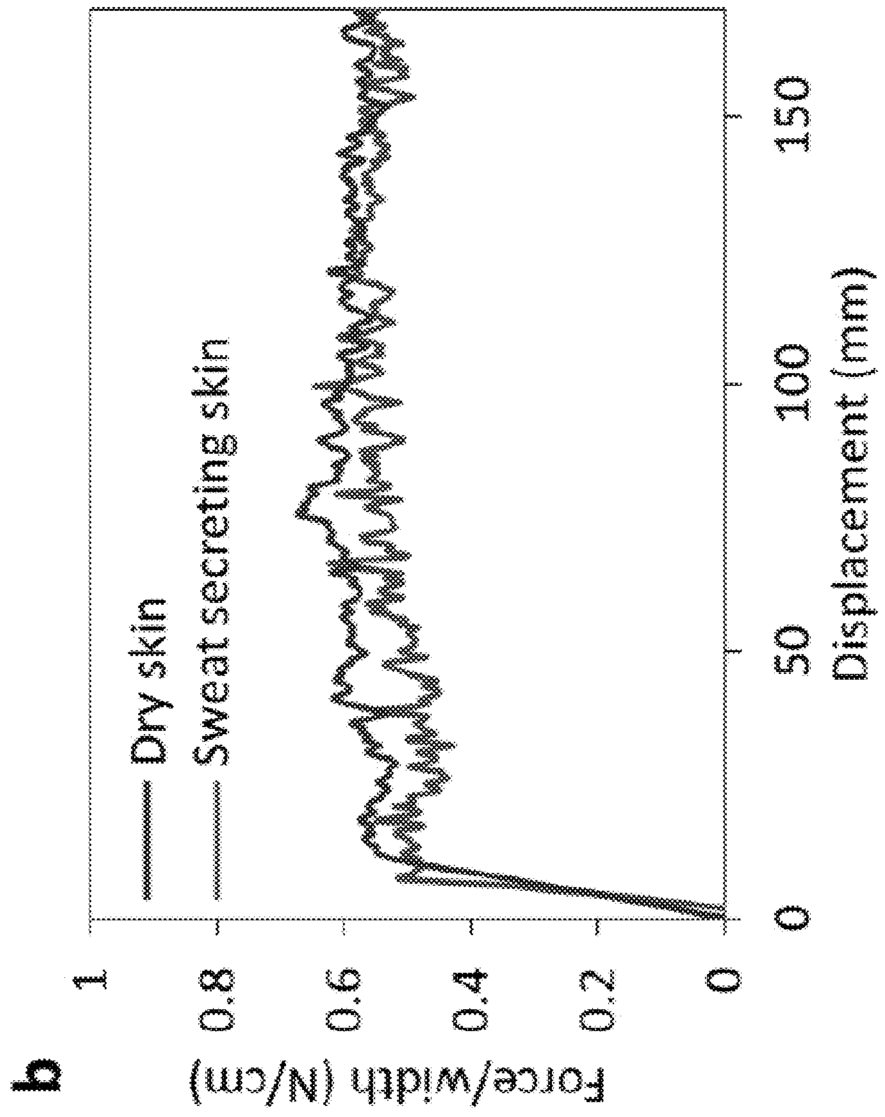
FIG. 11*b* illustrates exemplary characterization of the adhesion force between the skin-adhesive tape (bottom layer of the developed microfluidic device) and skin interface (performed on dry and exercise-induced sweat secreting skin). Exemplary results illustrate that adhesion forces are of similar strengths in both scenarios.
Figure 11A:
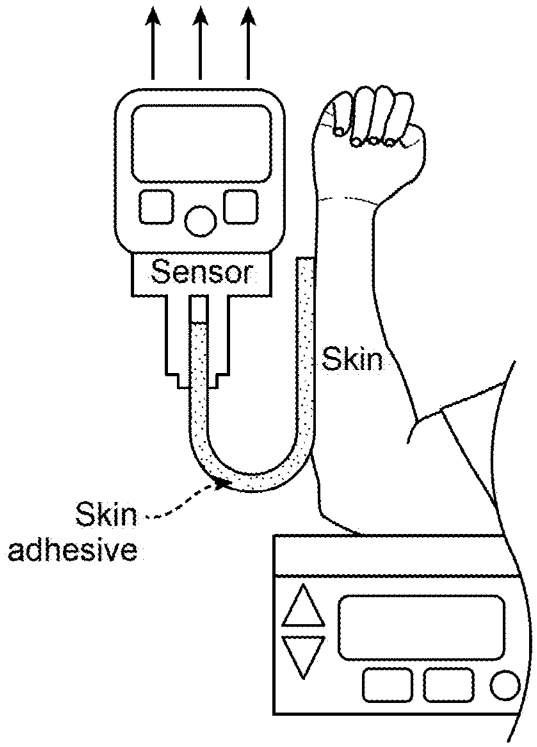

As shown in FIG. 5*d*, the exemplary wearable valve-enabled bioanalytical platform may be deployed for sweat sampling at scheduled and on-demand timepoints, to illustrate the platform's capability for contextually-relevant biomarker analysis applications. Accordingly, an exemplary platform may be mounted on the back of a subject engaged in cycling (with the aid of a skin-adhesive layer, which provides adequate adhesion force to maintain the platform on the skin, see FIG. 11 for example). Prior to on-body deployment, exemplary microheaters may be activated and electrical current passing through them applied to verify their operation. As can be seen from the on-body experiment, shown in FIG. 5*e*, the secreted sweat, at set scheduled/on-demand timepoints, may be routed to and compartmentalized within the desired compartments (following a 4-min microheater activation time-window), while other compartments may be protected. This time-stamped biofluid acquisition capability can be exploited to take contextual biomarker readings. As shown in FIG. 5*f*, the platform may be programmed to take glucose readings before and after a scheduled beverage intake (Trutol, containing 50 g/296 mL of dextrose) event, and sweat lactate level may be measured on-demand as per the user's command. Specifically, the exemplary biomarker readouts may indicate that the subject's sweat glucose level may be elevated after glucose intake, and the measured sweat lactate level may be within an expected range. FIG. 17 further illustrates suitability for compartmentalization and on-body operations of an exemplary sensor device. To provide physiologically meaningful interpretations of such sensor readouts, future large-scale studies may be conducted, aiming to contextualize the measured sweat biomarker concentrations in relation to relevant inter/intra-individual physiological variabilities (e.g., gender, muscle density, and body hydration).

Discussion

An exemplary programmable epidermal microfluidic valving system may achieve in-situ active biofluid management, which may be advantageous to the realization of autonomous and advanced biofluid processing and analysis capabilities underpinning the exemplary lab-on-body platforms. An exemplary microfluidic system includes network of individually-addressable microheater-controlled thermo-responsive hydrogel valves, fabricated following a high-throughput, low-cost, and scalable fabrication scheme. An exemplary electronic-hydraulic analogy provided the basis for developing a pressure regulation mechanism (integrated within the microfluidic valving system), which may be used to harvest biofluid, in-situ, from pressure-driven bio-interfaces (here, sweat glands). Exemplary wearable valving in the context of exercise-induced sweat sample compartmentalization, can include compartmentalization of iontophoretically induced sweat (where an exemplary secretion rate is on the same order as that of exercise-induced sweat). An exemplary dedicated programmable iontophoresis interface can also be integrated to enable contextually-relevant sweat sampling in sedentary subjects.

Exemplary active fluid control achieved by this system may be harnessed to create new wearable bioanalytical capabilities at both the sensor and system levels. At the sensor level, the valving capability may be exploited to decouple the previously overlooked issue (in wearable biosensing) of flow rate influence on sensor response. Accordingly, first, an exemplary mass transport-centered model may be formulated and presented within the framework of wearable microfluidic sensing, and subsequently, validated by simulation and experimental results. Then, to decouple the influence of flow rate, exemplary valving capability may be exploited to perform analysis in a sample-and-hold manner, allowing for obtaining undistorted biomarker readings. At the system level, addressable biofluid routing and compartmentalization achieved by valving may be leveraged to implement programmable sensor selection/protection. Through integration with a FPCB and seamless bilateral communication with consumer electronics, the valving system may be adapted for on-body biomarker analysis, where the exemplary capabilities may converge to render contextually-relevant (scheduled/on-demand) biomarker data acquisition.

The exemplary technology can be equivalently adapted to implement sample processing operations such as incubation, reagent delivery, and purification, thus enabling the realization of advanced assays (particularly, those in lab-on-a-chip settings) to create new biomarker detection solutions in a wearable format. The valve-enabled sample processing and analysis operations can be positioned as addressable compartments to form the building blocks of multi-step and multi-chamber bioanalytical functions within microfluidic architectures, allowing for the execution of synchronous/asynchronous sequential and parallel bioanalytical objectives autonomously. On a broader level, the convergence of the active biofluid management capabilities achieved by implementations in accordance with the presented implementations including those including active actuation modalities allows for the creation of fully autonomous lab-on-body platforms to monitor the biomarker profiles of individuals at the point-of-person, thus informing personalized and actionable feedback toward improving the individual's health.

Exemplary Methods

Figure 7:
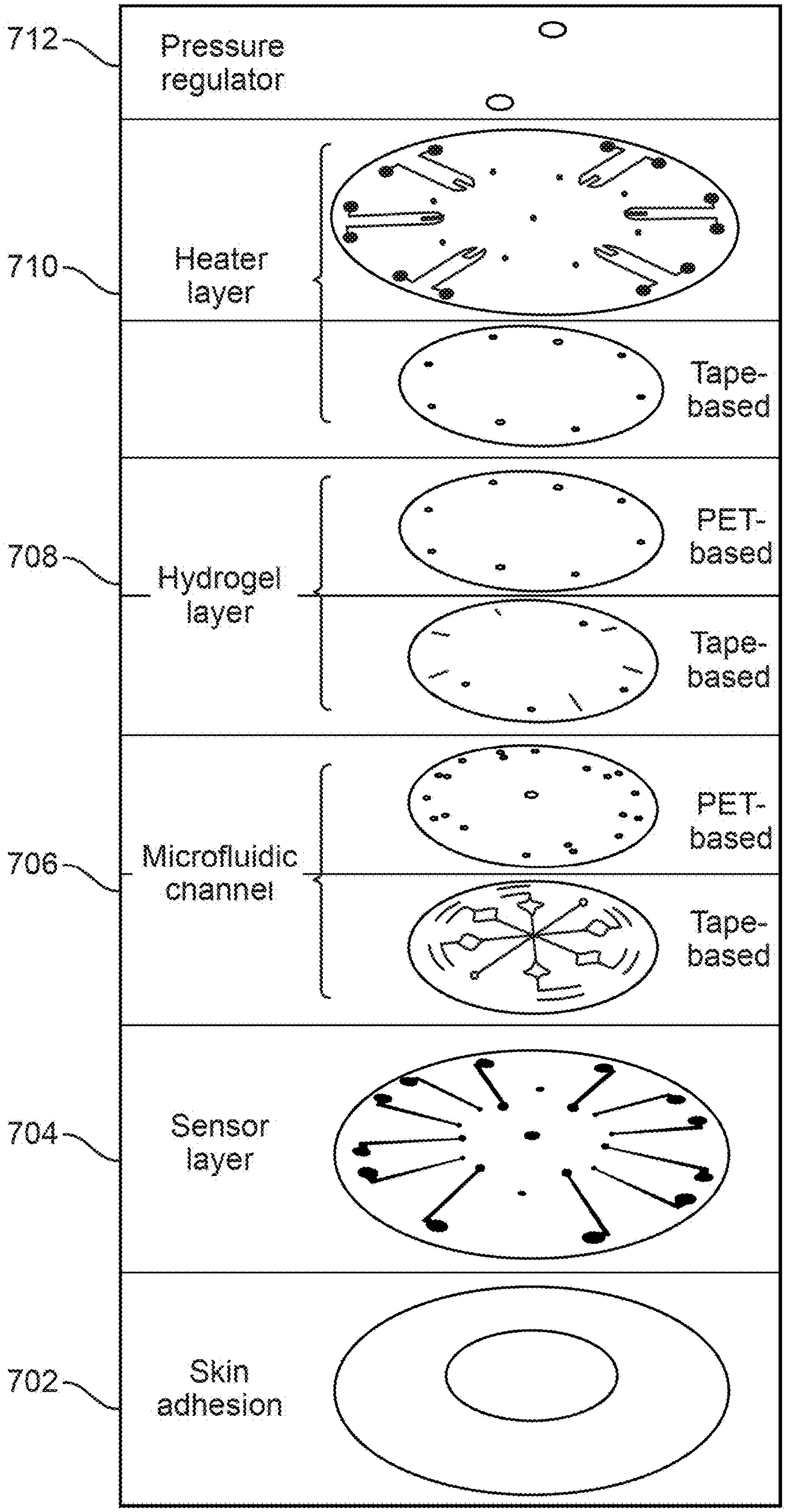
FIG. 7 illustrates an exploded view of an exemplary epidermal microfluidic valving system, which may be constructed by the vertical integration of pressure regulator/hydrogel implementations, laser-cut microfluidic channel layers, microheater/sensor array layers, and a double-sided adhesive skin adhesion layer.
Figure 8B:
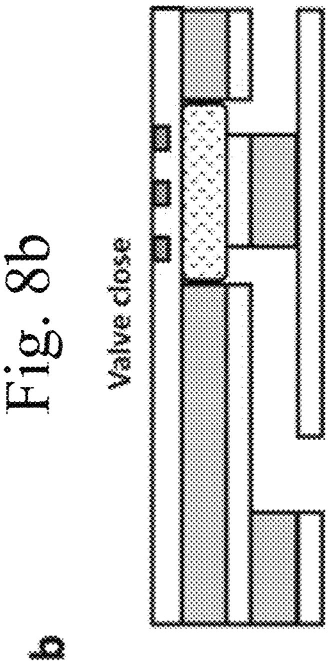
FIGS. 8*b* and 8*c* illustrate by way of example (b) valve closure when the microheater is off, and (c) valve opening when the microheater is on. In some implementations, microheater activation causes hydrogel shrinkage, allowing incoming biofluid to travel through the channel.
Figure 8C:
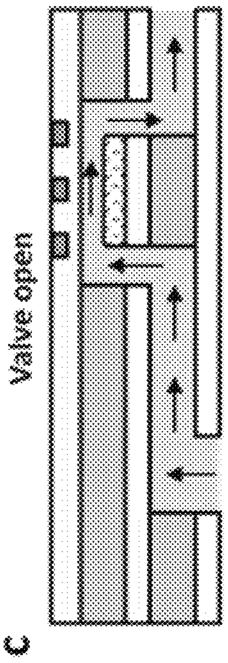
Figure 8A:
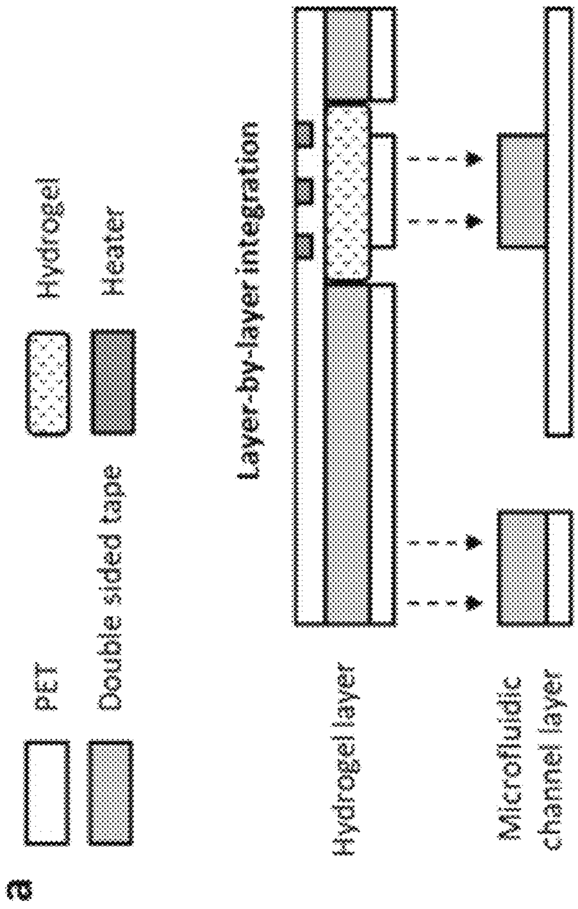
FIG. 8*a* illustrates an exemplary layer-by-layer integration method to form the valve interface.

One possible fabrication procedure of an exemplary wearable valve-enabled bioanalytical platform will now be described. As shown in FIG. 7, an exemplary wearable valve-enabled bioanalytical platform may be composed of multiple vertically stacked layers, which can be listed from the bottom to the top as: a double-sided skin adhesive film 702, a biochemical sensing electrode array 704 (e.g. for sensors 114) patterned on tape or a polyethylene terephthalate (PET, ~100 μm, MG Chemicals) substrate, a microfluidic layer 706 for sweat sampling, routing, and compartmentalization (e.g. channels 126), a thermo-responsive hydrogel array layer 708 (e.g. containing hydrogels 106), a microheater electrode array 710 for valve switching (e.g. for microheaters 110), and a pressure regulator 712 (e.g. 308). These components may be fabricated following the described protocols below:

Microfluidic module 706 may be constructed by vertical assembly of double-sided tapes (170 μm-thick, 9474LE 300LSE, 3M) and transparent PET film layers. Microfluidic features such as microchannels (e.g. 126) and VIAs (Vertical Interconnect Access) may be fabricated by laser-cutting (VLS2.30, Universal Laser Systems). Through vertical alignment of the microchannels and VIAs, fluidic connections may be made between different layers of the microfluidic module, rendering a 3D microfluidic structure.

Heater layer 710 and sensor electrode array 704 may be patterned on PET by photolithography using a positive photoresist (MicroChemicals AZ5214E), followed by the evaporation of 20 nm Cr, 100 nm Au, and 20 nm Ti. The sensor electrode array may be also patterned on PET by photolithography using positive photoresist (MicroChemicals AZ5214E), followed by the evaporation of 20 nm Cr and 100 nm Au. The lift-off step may be performed in acetone. To establish seamless electrical connections, in a spatially-efficient manner between the microheater/sensor array layers and the FPCB, double-sided adhesive anisotropic conductive films (ACFs, 9703, 3M, 50 μm) may be used as VIAs to connect the contact pads of the board (located on its front- and back-sides) to the layers. Specifically, for the microheater electrode array, the connections may be made to the front-side of the FPCB (from the top), and for the sensor electrode array, the connections may be made to the back-side of the FPCB (from the bottom).

Thermo-responsive hydrogels 106 included in a layer such as layer 706 may be prepared by mixing 0.545 g N-isopropylacrylamide (NIPAM, Sigma-Aldrich), 0.0297 g N,N'-methylenebisacryl-amide (Sigma-Aldrich), 0.75 mL dimethyl sulphoxide (Sigma-Aldrich), 0.25 mL deionized water, 0.02 mL [3-(methacryloylamino)propyl]trimethylammonium chloride (MAPTAC, Sigma-Aldrich) solution (50 wt. % in water), and 0.0385 g 2,2-dimethoxy-2-phenylacetophenone (DMPA, Sigma-Aldrich). This mixture may then be sonicated in a water bath for 30 minutes at 48° C. with a sonication frequency of 40 kHz. Next, the mixture may be injected and cast into custom-designed tape-based molds (laser-cut with the desired features), followed by a photo-polymerization step (405 nm ultraviolet light, Formlabs Form Cure, intensity: 1.25 mW/cm$^2$ and exposure time: 2 minutes). The crosslinked hydrogels may be immersed in a DI water bath for at least 12 hours, prior to their deployment for the planned characterization/validation experiments.

Pressure regulator 712 may be constructed by embedding laser-cut filter membranes (GD 120 Glass Fiber Filter, Advantec MFS Inc.) in between two double-sided tape layers (170 μm-thick, 9474LE 300LSE, 3M), forming a sandwiched structure. Epoxy (Devcon) may be used to seal the gap between the layers.

Platinum-based working electrodes in biochemical sensing layer 704 may be constructed by electrochemically depositing (−0.1 V versus Ag/AgCl, 600 s) a platinum nanoparticle (PtNP) layer onto the designated sensor electrodes (Au-based) using an aqueous solution containing 2.5 mM Chloroplatinic acid ($H_2PtCl_6 \cdot 6H_2O$, Sigma-Aldrich) and 1.5 mM formic acid (Sigma-Aldrich). Next, a poly-m-phenylenediamine (PPD) layer may be electrochemically deposited onto the PtNP/Au electrode (0.85 V versus Ag/AgCl, 300s) in a phosphate-buffered saline (PBS) solution (pH 7.2; Gibco PBS, Thermo Fisher Scientific) containing 5 mM m-phenylenediamine (Sigma-Aldrich). The constructed PPD/PtNP/Au electrode may then be washed (with DI water) and dried at room temperature. Reference electrodes may be constructed by drop-casting Ag/AgCl ink onto the designated electrodes (Au-based). Then, the deposited layer may be dried at 70° C. for 30 min. Exemplary Ag/AgCl reference electrode construction may take place in between the PtNP and PPD deposition steps (when constructing the working electrode).

To develop an exemplary glucose sensor for layer 704, 0.3 μL of a 1:1 (v/v) mixture of 1% chitosan solution and glucose oxidase (50 mg/ml in PBS, pH 7.2; Sigma-Aldrich) may be coated onto the PPD/PtNP/Au electrode (1.13 mm2). The 1% chitosan solution may be prepared by dissolving chitosan (Sigma-Aldrich) in a 2% acetic acid (Sigma-Aldrich) solution at 60° C. for 30 min. To develop the lactate sensor, a 0.3 μL of 1:1 (v/v) mixture of bovine serum albumin (BSA, Sigma-Aldrich) stabilizer solution and lactate oxidase solution (50 mg/ml in PBS, pH 7.2; Toyobo) may be coated onto the PPD/PtNP/Au electrode (1.13 mm2) and dried at room temperature for 1 hour. The BSA stabilizer solution may be prepared by adding 0.8% (v/v) of 25 wt % glutaraldehyde solution (GAH, Sigma-Aldrich) in a PBS solution containing 10 mg/ml BSA. Then 0.3 μL of PVC solution (0.375 wt % in Tetrahydrofuran; Sigma-Aldrich) may be deposited twice (separated by 1 hour) onto the electrode surface to form a lactate diffusion limiting layer. All sensors may be allowed to dry overnight at 4° C. while being protected from light, prior to their deployment for the planned characterization/validation experiments.

To characterize exemplary effect of temperature on hydrogel shrinkage, an exemplary circular hydrogel may be placed on top of a hot plate (Isotemp, Fisher Scientific). The temperature of the hot plate may be gradually increased, with 2° C. temperature increments and 2 minutes of wait time (allowing the hydrogel to reach steady state). In order to characterize the fabricated microheater-coupled hydrogel's reversible response, a DC power supply (Keithley 2230-30-1, Keithley Instruments Inc.) may be used to apply 2.8 V across the microheater electrodes. This configuration allows for immediate delivery and removal of heat, and the characterization of the hydrogel's transient volumetric transition. Optical imaging may be performed, followed by image analysis, to quantify the changes in the area of the hydrogel.

As shown in the example of FIG. 2*c*, to characterize the flow control capability of the hydrogel valve, the inlet of a valve-gated microfluidic channel may be connected to a Proportional-Integral-Derivative (PID) controlled syringe pump (PHD ULTRA™ CP, Harvard Apparatus), which may be configured to maintain a pressure of 15 mmHg with a flow rate range of 0 μL/min to 10 μL/min. To control the syringe pump, via a feedback loop, the test device inlet pressure may be measured and transduced with the aid of a pressure sensor (Blood Pressure Transducers, APT 300, Harvard Apparatus) and a transducer amplifier module (TAM-D, Harvard Apparatus). In some implementations, flow rate data during periodic valve activation/deactivation is recorded by PID Pump Data Log software (Harvard Apparatus) and processed by applying a Savitzky-Golay filter to remove measurement artefacts (e.g., pump's mechanical noise). Furthermore, near-zero readings (processed PID system data) correspond to a zero flow rate when the valve is closed, in some implementations.

Three microfluidic test device configurations may be used to correspondingly characterize the device breakage pressure, valve open pressure, and adjusted pressure by the regulator: 1) a microfluidic channel with a closed embedded valve; 2) a microfluidic channel with an open embedded valve; and 3) a microfluidic channel with an auxiliary pressure regulator channel. In separate experiments, each configuration may be connected to a syringe pump, which may be programmed to inject a solution at the constant flow rate of 5 μL/min into the test device's channel. Specifically, in order to characterize the valve's maximum tolerable pressure ($P_{max}$), where the first device configuration may be used, the solution may be continuously injected until the device breakage occurred (evident from a drop in the measured pressure). The corresponding pressures across the inlet and outlet of the channels of the test devices may be measured by a pressure sensor (Blood Pressure Transducers) and recorded by the PID Pump Data log software (Harvard Apparatus).

To assess the operational fidelity of the exemplary valving system, six-compartment pressure-regulated microfluidic valving devices such as those shown in FIG. 3*h* may be tested for stability under induced motion artifacts and prolonged use. For both cases, the devices' inlets may be connected to the aforementioned flow control characterization setup, which allowed for continuous solution injection and device flow rate monitoring. During the valve activation/deactivation, the flow rate data may be recorded, and subsequently post-processed with the aid of the PID Pump Data Log software and filters. To test for prolonged valving operation, a designated compartment may be sequentially activated and deactivated at set timepoints over a period of 6 hours. For the motion artifacts test, an accelerometer (on a smartphone) may be affixed to the device and a vortex mixer (Fisher Scientific), which may be adjusted to mimic 3D oscillatory acceleration conditions (amplitude: ~3 $m/s^2$ at 5 Hz generated by a vortex mixer).

To characterize the response of exemplary developed enzymatic sensing interfaces (see exemplary chemical compositions in Table 2 below), amperometric measurements may be performed at +0.5 V versus Ag/AgCl in the sample solution (e.g., glucose and lactate) with a potentiostat (CHI 660E, CH Instruments). Calibration plots of glucose and lactate sensors may be obtained by recording the amperometric responses in a series of PBS solution containing different concentrations of the target analytes (D-(+)-Glucose: from 50 μM to 400 μM, Sodium L-lactate: from 2 mM to 10 mM, Sigma-Aldrich). To investigate exemplary flow rate effect on the sensor performance, amperometric responses may be recorded while continuously injecting the PBS solution containing 200 μM glucose into the glucose sensing chamber with the flow rate incrementally ramping up from 2 to 10 μL/min (controlled by a syringe pump, Harvard Apparatus).

TABLE 2

| Chemical name | Deposition method | Function/Role |
|---|---|---|
| Gold (Au) | E-beam deposition | Electron transfer |
| Platinum nanoparticle (PtNP) | Electrodeposition | Electrochemical catalyst/ electron transfer |
| Enzymatic layer (Glucose- and lactate-Oxidase) | Drop casting | Glucose catalysts (enzyme activity: 100-250 units/mg) Lactate catalyst (enzyme Activity: ~100 units/mg) |
| Polyvinyl chloride (PVC) | Drop casting | Diffusing limiting layer (only for the lactate sensor) |

Finite element analysis (FEA) of the flow rate influence on sensor response may be performed as follows. FEA software such as COMSOL 5.2 may be used to simulate the concentration profile of a model analyte inside a microfluidic channel under various laminar flow rate conditions. In the simulation software, two simulation packages, "laminar flow" and "transport of diluted species", may be employed and coupled in the context of a 2D microfluidic channel. The channel may be set to be 170 μm in height, which may be the same as the experimental setup. The sensor (1 mm in length) may be positioned far enough from the inlet, allowing for the establishment of a pressure-driven Poiseuille flow profile. Input average flow velocities may be determined in relation to the experimentally relevant volumetric flow rate (1-10 μL/min) and by assuming a channel height of 170 μm and width of 2 mm. In some implementations, a range of volumetric flow rate is selected based on previously reported active sweat secretion rates and device sweat collection area (8 $cm^2$). Exemplary analyte bulk concentration at the inlet of microfluidic channel ($c_0$) may be set to 200 μM and the concentration at the sensor surface may be set to zero (following the high surface reaction rate assumption). The diffusion coefficient of target analyte (here, glucose) may be set as $6.7\times10^{-6}$ $cm^2/s$. The exemplary concentration gradient of the analyte at the vicinity of the sensor surface (at its midpoint) may be extracted to infer the analyte flux onto the sensor.

In some implementations, COMSOL 5.2 can simulate mechanical behavior of an exemplary developed microfluidic valve device under bending conditions. A representative 2D model of a microfluidic valve (cross-view) for mechanical analysis assumes no delamination between layers/components being considered. Bending force can be applied on the bottom PET layer with the vertical displacement of the two corners set to zero. The magnitude of the force can be adjusted based on the simulated bending curvature. An exemplary modelled device's geometric and mechanical properties are based on those of a corresponding fabricated device.

Exemplary wireless addressable valving and biomarker analysis may be realized with a custom-developed FPCB such as that shown in FIGS. 5*c*, 9 and 10. An on-board MCU 502, with the aid of analog multiplexers 508, may be utilized to select the desired channels for valve actuation (via activating the microheater) and signal acquisition from the corresponding sensors. The selection of the valves results in the electrical connection of the designated microheater 110 contact pads with a programmable current source 520. The selection of the sensing channels results in the electrical connection of the designated sensing electrodes' 114 contact pads with a potentiostat chip. The potentiostat chip (in analog front end (AFE) 514) may be programmed to apply 0.5 V across the working and the reference electrodes, and to convert the acquired sensor current signal to voltage through the internal transimpedance amplifier. The processed signal by the potentiostat may then be filtered by a fifth-order low-pass filter (in AFE 514) with a cutoff frequency of 1 Hz and translated into the digital domain with the aid of the MCU's built-in 10-bit analog-to-digital converter. By interfacing the MCU 502 with a Bluetooth® module 594, wireless, bilateral, and real-time communication of user commands and sensor output data with Bluetooth®-enabled consumer electronics may be achieved (e.g., smartphone or smartwatch).

A smartwatch application may be developed to implement a user-friendly interface for programming biomarker acquisition timepoints (scheduled or on-demand). An intermediary smartphone, pre-loaded with a programmed operating system, may be used to mediate the smartwatch and FPCB communication, and to store data. An exemplary smartwatch application features three main functions, namely: "History", "Scheduled", and "On-demand." These functions are accessible through a main selection screen that also displays the current time. In some implementations, a "History" function stores and displays most recently recorded biomarker data in the format of a time series bar chart, based on the data stream received from the FPCB module, via Bluetooth®). An exemplary "Scheduled" function displays the defined schedule for biomarker recording. This function can also transmit sensor selection activation command (an integer index between 1 to 6) to the FPCB module (via Bluetooth®) in accordance to the defined schedule. The "On-demand" function overrides the schedule and to transmit the sensor selection activation command on-demand. This function features a scrolling list from which the user can select the desired sensing compartment. An intermediary smartphone, pre-loaded with a programmed Android service, can be used to mediate the smartwatch and FPCB communications for data storage.

Figures 18A, 18B:
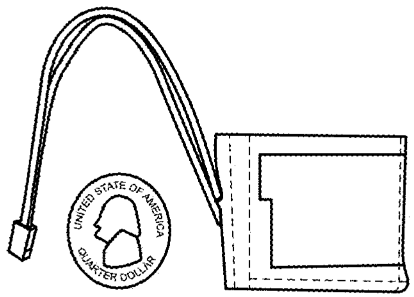
FIG. 18*a* illustrates exemplary power requirements for exemplary electronic components.
FIG. 18*b* illustrates an exemplary rechargeable lithium-ion polymer battery module used to power an exemplary FPCB module (placed next to the Washington quarter for visual comparison).

An exemplary custom-developed wireless FPCB is powered by a single rechargeable lithium-ion polymer battery with a nominal supply voltage of 3.7 V as shown in FIG. 18. This FPCB features a power management module that utilizes a voltage regulator chip to provide a stable voltage level of 3.3 V, to power up the rest of the circuit modules such as those shown in FIGS. 9 and 10. An exemplary system draws on an average of 9 mA from the battery when no heater is on and 109 mA when activating a heater. Battery capacity and discharge current ratings are modifiable depending on exemplary modes, duration, and frequency of operations. In one example such as that shown in FIG. 5*c*, in a trial lasting 3 hours, sweat sampling and analysis are performed at 3 timepoints (each valve activation over 4 min), a battery with a capacity rating on the order of 48.8 mAh (=109 mA×0.2 h+9 mA×3 h) and discharge capability on the order of 100 mA are needed—the requirements that can be met by the lithium-ion polymer batteries widely used in commercialized wearable technologies (e.g., smartwatches).

The flexibility and the adhesive surface of the exemplary constructed devices allows for their placement on various body parts. To validate sweat sampling, routing, compartmentalization, and analysis, the developed devices may be mounted onto the back of a healthy adult male volunteer engaged in cycling sessions. Prior to on-body application, the microheaters' operations may be verified by monitoring the current passage through the designated microheater electrodes. Some implementations include thermocouple wires at the device/skin interface where effect of microheater activation on skin temperature is minimal (<4° C.). Additionally, exemplary sensors can be pre-calibrated. To visualize sweat sampling, blue dyes (FD&C Blue) may be embedded within the constructed compartments. For on-body sweat glucose analysis, the subject may be scheduled and instructed to consume a high-glucose beverage (Trutol, containing 50 g/296 ml of dextrose) in between two exercise sessions. Here, the device may be programmed to activate the "glucose analysis" valves before and after beverage intake. For on-body sweat lactate analysis, the subject manually activated the corresponding valve at an unscheduled timepoint (representing on-demand device operation). For each analysis, sweat sampling may be performed over a period of four minutes (after activating the valve), and biomarker analysis may be performed for 100 seconds when the valve may be turned off.

Supplementary Discussion

Exemplary analysis of the flow rate influence on the electrochemical sensor response. In the exemplary general case of modeling the response of a microfluidic electrochemical sensing system, analyte transport (by advection and diffusion) and surface reaction may be simultaneously considered. However, in the context at hand, because of the high enzymatic catalytic activity (i.e., high surface reaction rate), it can be assumed that the response of the electroenzymatic sensor may be completely controlled by analyte transport onto the sensor surface1. Accordingly, the enzymatic current response can be presented as $$I = nFAJ \qquad (1)$$

where n is the number of electrons in the electro enzymatic reaction, F is Faraday's constant, A is the sensing electrode area, and J is the analyte flux (molecules per area per time) onto the sensor surface.

When no flow rate is present, the analyte consumption on the sensor surface creates a growing analyte depletion zone with a thickness of $\delta \propto \sqrt{Dt}$, where D is the diffusion coefficient of the target analyte and t is time. Accordingly, the analyte molecules diffuse along the concentration gradient, resulting in analyte flux J onto the sensor surface, where J=D $\nabla_c$. As the first-order approximation, the gradient $\nabla_c$ can be simply equated to the difference in the analyte concentration in bulk ($c_0$) vs. immediate vicinity of the sensor surface ($c_s$, where $c_s \approx 0$ due to the assumption of relatively high surface reaction rate) divided by the depletion thickness ($\delta$), hence:

$$J \approx \frac{D(c_0 - c_S)}{\delta} \approx \frac{Dc_0}{\delta} \qquad (2)$$

Despite the continuous growth of the depletion thickness with time, with measurements at a fixed timepoint, the proportionality of J in relation to $c_0$ can be exploited to establish a linear calibration curve (current response vs. analyte concentration, e.g., FIGS. 4*b* and 4*c*). When performing sensing in the presence of advective flow (with volume flow rate Q) inside a microfluidic chamber, because of the continuous supply of analytes, the advection may halt the growth of the depletion zone, setting a steady-state $\delta_s$. For the case where the advection transport may be stronger than analyte diffusion (captured by the non-dimensional Peclet number, $$Pe = \frac{Q}{DQ} \gg 1\bigg),$$

the advective delivery of analytes may result in the compression of the depletion zone following the relationship below:

$$\frac{\delta_s}{L} \sim \sqrt[3]{\frac{DH^2W}{QL^2}} \qquad (3)$$

Here, L is the length of the sensor and W and H are the chamber width and height, respectively. Combining equations (1-3) yields $I \propto J \propto \sqrt[3]{Q}$, as illustrated by way of example in both the simulation and experimental results (FIGS. 4*e* and 4*f*).

Further Exemplary Methods

A Stimuli-responsive Hydrogel Array Fabrication Scheme for Large-scale and Wearable Microfluidic Valving. In some implementations, programmable microfluidic valving enables controlled routing and compartmentalized manipulation of fluid within networks of microfluidic channels-capabilities which can be harnessed to implement an automated, massively parallelized, and diverse set of bioanalytical operations in large-scale microfluidics (lab-on-a-chip) and wearable (lab-on-the-body) applications. In some implementations, stimuli-responsive hydrogels are suitable base materials to construct programmable microfluidic valving interfaces: once embedded in a microfluidic channel, their volumetric shrinkage/expansion (in response to stimulus) can be exploited to open/close microfluidic channels. Advantages of exemplary fabrication include robustness (e.g., complete channel sealing), scalability (forming arrays of valves with high yield and throughput), miniaturization of the valve actuation interface, and mechanical compatibility (flexibility for wearability). In some implementations, a simple and low-cost fabrication scheme creates arrays of stimuli-responsive hydrogels (e.g., thermo-responsive) and optional stimulus embodiments (e.g., microheaters) with compact footprints and within complex microfluidic networks. This exemplary fabrication scheme 1) introduces an ex situ hydrogel hydro-conditioning step to achieve full channel sealing; 2) optimizes the valve performance to achieve maximal volumetric response; and 3) utilizes mechanically flexible and thin device layers to ensure compatibility for wearable applications. In some implementations, scalability of fabricated valves and their enabling microfluid management capabilities demonstrate fluid routing/compartmentalization within valve-gated square matrix and radial tree matrix microfluidic networks. Conventional valves fabricated are operationally incompatible for large-scale microfluidics and wearable applications due to inevitable needs for buffer exchange (to replace the hydrant solution with biofluid sample solution) and hydrant solution storage/delivery. Both incompatibilities can complicate design and operation of the device, limiting the scalability of the device.

In some implementations, to position hydrogel valves for large-scale microfluidics and wearable applications, a simple and low-cost fabrication scheme allows for creating arrays of stimuli-responsive hydrogels, embedded within complex and mechanically flexible microfluidic networks with compact footprints. In some implementations, poly(N-isopropylacrylamide) (PNIPAM) hydrogel is thermally actuated via miniaturized heating elements. In some implementations, thermal actuation includes heating elements on a circuit board interfacing the microfluidic module, or by microheaters directly integrated with the microfluidic module. In some implementations, scalability of the fabricated valves and their enabling microfluid management capabilities is driven by fluid routing/compartmentalization within various microfluidic configurations.

Figure 19A:
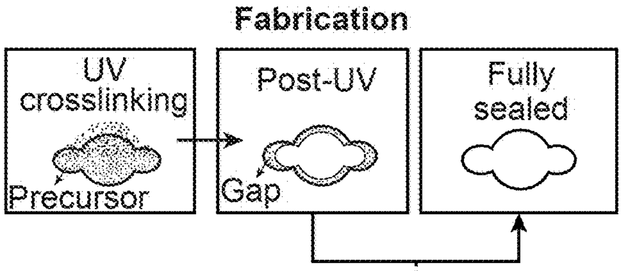
FIG. 19*a* illustrates exemplary fabrication of a stimuli-responsive hydrogel-based valve. In some embodiments, a one-step hydrogel hydro-conditioning step, in, for example, deionized (DI) water is performed after UV crosslinking and prior to the incorporation of the hydrogel in the channel to ensure full channel sealing.
Figure 19C:
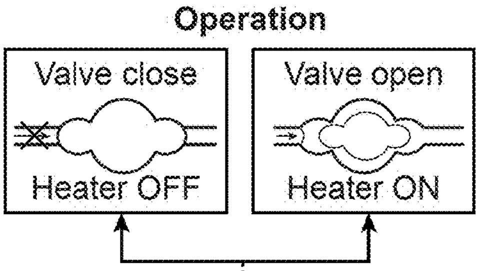
FIG. 19*c* illustrates exemplary schematic operation of a PNIPAM hydrogel valve: activation of the heater results in hydrogel shrinkage, opening of the channel, and permitting the fluid flow.
Figure 19B:
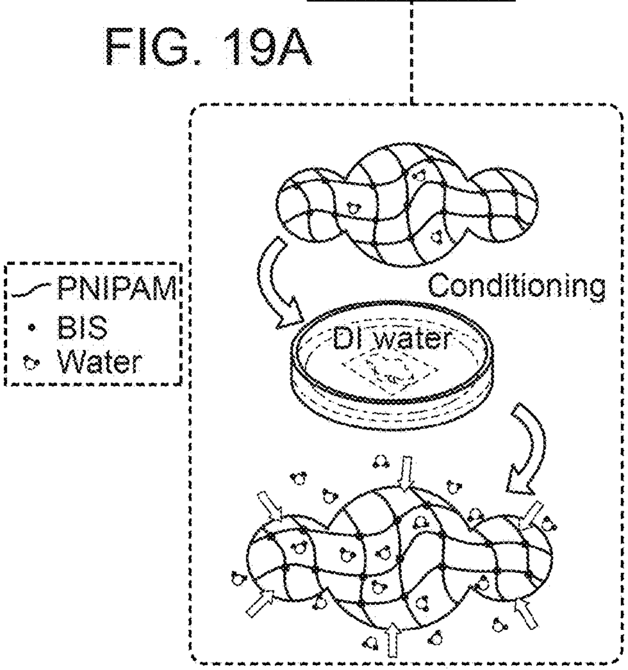
FIG. 19*b* illustrates exemplary expansion of a hydrogel due to infusion of water molecules.
Figure 19D:
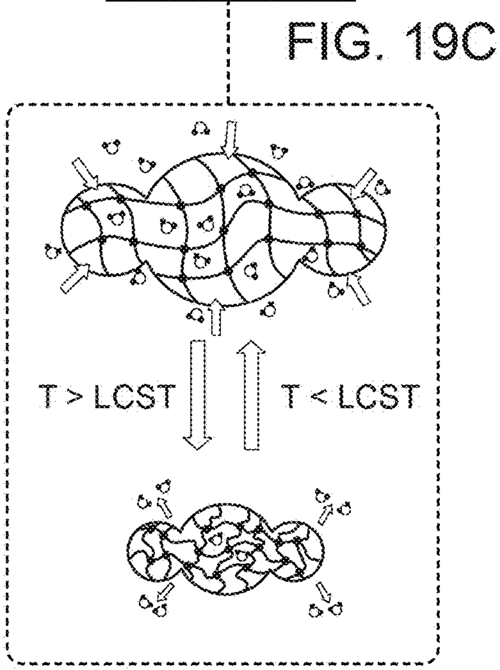
FIG. 19*d* illustrates exemplary PNIPAM hydrogel shrinkage and expansion upon adjusting temperature above and below the hydrogel's LCST.

In some implementations, stimuli-responsive hydrogel valve array fabrication includes 1) laser-patterning polyethylene terephthalate (PET)/double-sided tape substrates to define 2D valve and channel features in designated "valve" layer and "microfluidic channel layers" (as two separate layers), respectively; 2) polymerizing hydrogel in situ (with optimized crosslinker concentration), via exposing the valve layer to ultraviolet (UV) light as shown in FIG. 1*a;* 3) hydro-conditioning the valve layer to achieve hydrogel expansion (due to infusion of water molecules), and render full channel sealing as shown in FIG. 19*b*; and 4) aligning and integrating the open-face valve and microfluidic channel layers to vertically connect the 2D fluidic pathways between the two layers, realizing a complete valve-gated microfluidic channel. In some implementations, fabrication includes constructing a valve using the thermo-responsive PNIPAM hydrogel, which reversibly shrinks and expands in response to temperature increase/decrease around its lower critical solution temperature (LCST), as illustrated by way of example in FIGS. 19*c* and 19*d.*

Figure 19E:
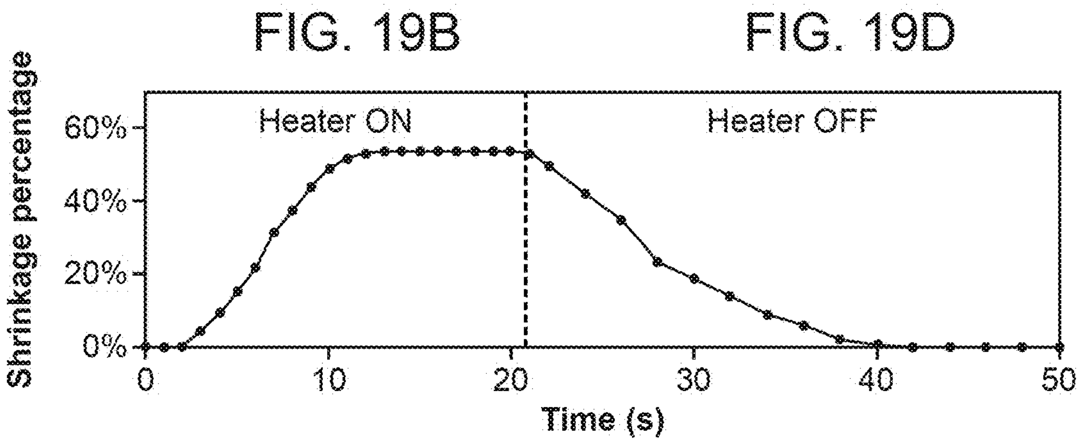
FIG. 19*e* illustrates exemplary characterization of a representative PNIPAM hydrogel's temporal volumetric response to the activation and deactivation of the heater.

In some implementations, a reversible thermo-responsive property of the PNIPAM hydrogel originates from the temperature-tunable interactions between water molecules and the hydrophilic amide group/hydrophobic propyl group within its polymer structure. As shown by way of example in FIG. 19*e*, in the context of temperature change induced by a local heater, the PNIPAM-based hydrogel can shrink 55% when activating the heater and restored to its initial size when deactivating the heater.

An exemplary valving performance, with regards to channel sealing (when valve closed), is illustrated in FIG. 20*a*. As illustrated in FIG. 20*b*, an exemplary ex situ hydro-conditioning step results in increasing the valve's back pressure (maximum pressure that the valve can hold without any leakage) by more than 15 times. In some implementations, to achieve the highest degree of valving opening, the shrinkage percentage of the hydrogel can be optimized by adjusting the crosslinker concentration (N,N'-methylenebisacrylamide, BIS). As shown by way of example in FIG. 20*c*, an exemplary hydrogel with 4% crosslinker exhibited the highest shrinkage (~55%), as compared to 8% and 16% cases. FIG. 20*c*'s insets show corresponding exemplary scanning electron microscopy (SEM) images of the hydrogels with different crosslinker concentrations. Exemplary valve-gated microfluidic channel flow, shown by way of example in FIG. 20*d*, includes fluid flow completely blocked with no leakage (flow rate: 0 μL/min) when the valve is deactivated, and fluid flow permitted when the valve is activated (flow rate: 10 μL/min).

Figure 21:
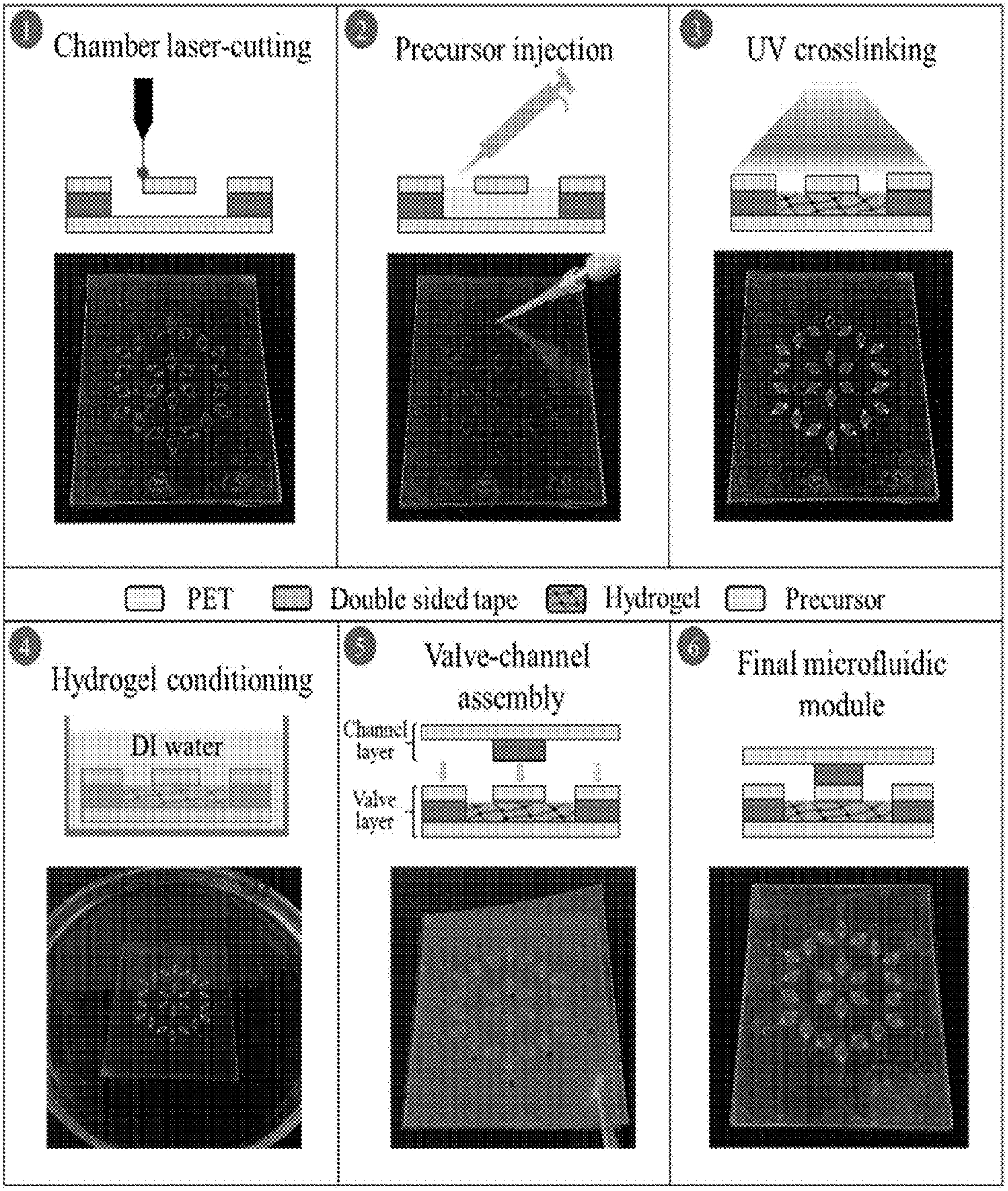
FIG. 21 illustrates exemplary fabrication of a hydrogel valve-gated microfluidic network. In some implementations, hydrogel valve array and microfluidic channel features are patterned by laser-cutting (~10 μm precision) the valve and channel layers. In some implementations, the PNIPAM precursor solution is injected into the designated valve chambers (on the valve layer) through the vertical openings, and then polymerized via UV crosslinking. In some implementations, the hydrogel array is conditioned via immersion of the valve layer in DI water for 12 hours. In some implementations, the open-face valve and channel layers are vertically aligned and assembled. PET thickness: 100 μm, PET flexural modulus: 3380 MPa, double-sided tape thickness: 170 μm. The size of the valve is 5 mm (axially).

An exemplary fabrication is illustrated by way of example in FIG. 21. In some implementations, rendering valve/channel features with micrometer-spatial resolution within disposable, thin, and mechanically flexible microfluidic modules, makes a resulting device suitable for constructing both large scale microfluidics and wearable platforms.

Figure 22A:
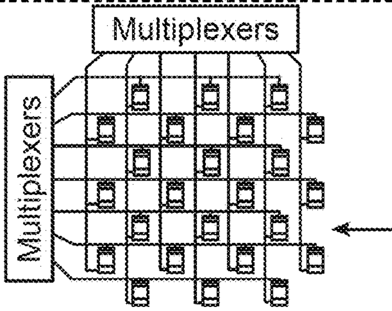
FIGS. 22*a*-22*f* illustrate aspects of an exemplary device.
Figure 22B:
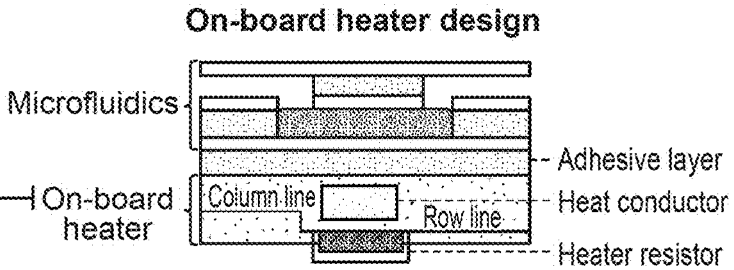
Figure 22C:
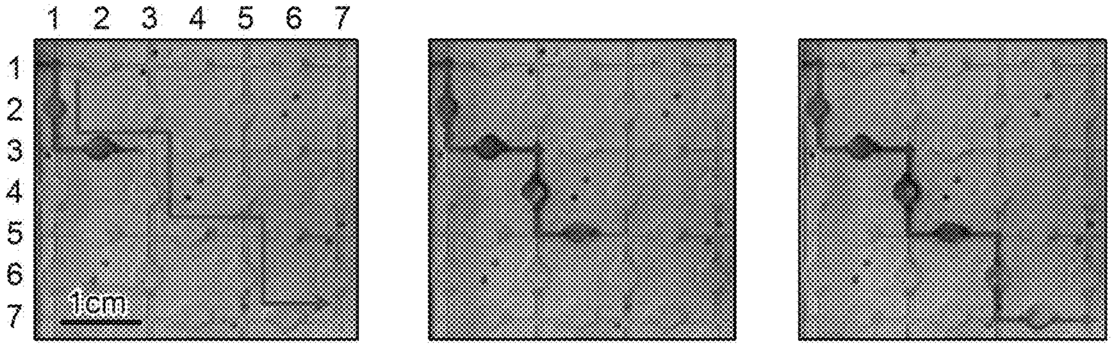
Figure 22D:
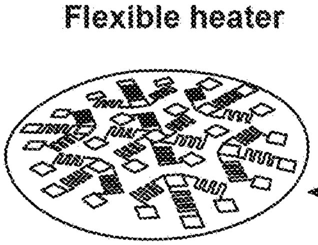
Figure 22E:
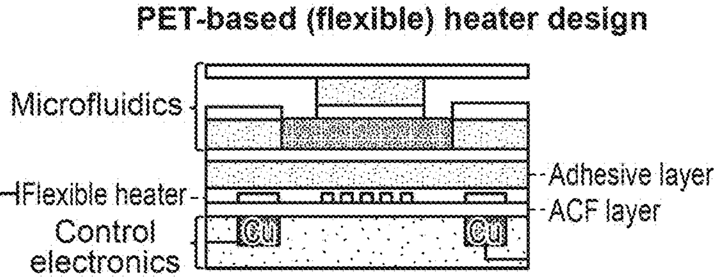
Figure 22F:
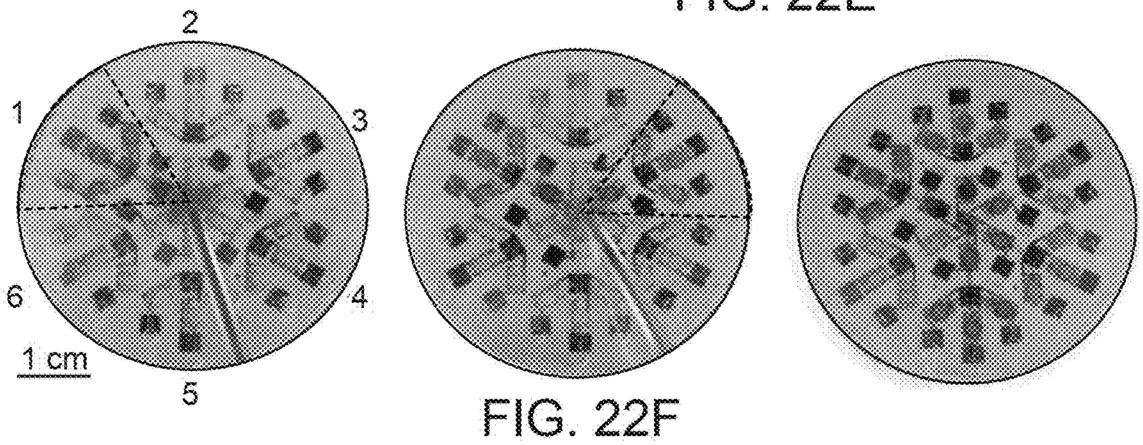

Fluid routing and compartmentalization within valve-gated complex microfluidic networks will now be described. Exemplary PNIPAM hydrogel valve arrays can be thermally actuated via addressable miniaturized heating elements. In some implementations, valve arrays in large-scale microfluidic and wearable applications include addressable actuation interfaces of: 1) a multi-layered printed circuit board, featuring highly dense heating elements, connected to control programmable circuitry as shown in FIGS. 22*a-c*, and 2) a flexible substrate (PET), directly integrated within the microfluidic module, forming a fully flexible device as shown in FIGS. 22*e-f.* In some implementations, biofluid routing and compartmentalization are realized within a valve-gated square matrix and a radial tree matrix microfluidic network.

In some implementations, a simple and low-cost fabrication scheme creates stimuli-responsive hydrogel valves, addressing fabrication challenges, such as robustness and scalability. In some implementations, an exemplary devices includes a thermo-responsive hydrogel. In some implementations, a device includes thermo-responsive hydrogel valve arrays-coupled with actuation interfaces (on-board/flexible microheaters)—within complex microfluidic networks. In some implementations, biofluid management capabilities (e.g., fluid routing and compartmentalization) can be adapted to implement automated, massively parallelized, and diverse bioanalytical operations in large-scale microfluidics (lab-on-a-chip) and wearable (lab-on-the-body) applications.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A device comprising:

a microfluidic layer having a plurality of compartments;

a hydrogel layer comprising a plurality of thermo-responsive hydrogel valves corresponding to the plurality of compartments, wherein the thermo-responsive hydrogel valves have a transition temperature equal to or greater than 45° C.;

an electrode layer comprising a plurality of sensors respectively corresponding to the plurality of compartments; and a plurality of pressure release mechanisms respectively configured to regulate hydraulic pressure in the plurality of thermo-responsive hydrogel valves and corresponding plurality of compartments.

2. The device of claim 1, further comprising a heater layer, wherein the heater layer is patterned to comprise a plurality of microheaters, each of which is configured to selectively apply heat to a respective one of the plurality of thermo-responsive hydrogel valves.

3. The device of claim 2, wherein the heater layer further comprises a tape-based layer.

4. The device of claim 1, further comprising a skin adhesion layer.

5. The device of claim 1, wherein the microfluidic layer further comprises at least one of a polyethylene terephthalate (PET) based layer and a tape-based layer.

6. The device of claim 1, wherein the hydrogel layer further comprises at least one of a polyethylene terephthalate (PET) based layer and a tape-based layer.

7. The device of claim 1, wherein the microfluidic layer defines channels between the plurality of compartments having a serial architecture.

8. The device of claim 1, wherein the microfluidic layer defines channels between the plurality of compartments having a parallel architecture.

9. The device of claim 1, wherein the microfluidic layer defines channels between the plurality of compartments having a tree architecture.

10. The device of claim 1, wherein one of the plurality of sensors is configured to sense glucose in biofluid, and wherein another of the plurality of sensors is configured to sense lactate in biofluid.

11. The device of claim 10, wherein the biofluid comprises sweat.

12. The device of claim 1, wherein the thermo-responsive hydrogel comprises poly(N-isopropylacrylamide) (PNIPAM).

13. The device of claim 1, wherein the thermo-responsive hydrogel comprises an ionizable monomer.

14. The device of claim 13, wherein the ionizable monomer comprises 3-(methacryloylamino)propyl]trimethylammonium chloride (MAPTAC).

15. The device of claim 1, wherein the plurality of thermo-responsive hydrogel valves each have a maximum tolerable pressure, and wherein the plurality of pressure release mechanisms are respectively configured to prevent hydraulic pressure to exceed the maximum tolerable pressure.

16. The device of claim 1, wherein the plurality of thermo-responsive hydrogel valves each include a secondary conductive path for redirecting fluid flow as a relief mechanism.

17. The device of claim 1, wherein the plurality of thermo-responsive hydrogel valves each include a membrane filter incorporated within an auxiliary microfluidic channel to render a desired hydraulic resistance.

* * * * *